United States Patent [19]
Grahn

[11] Patent Number: 5,604,314
[45] Date of Patent: Feb. 18, 1997

[54] TRIAXIAL NORMAL AND SHEAR FORCE SENSOR

[75] Inventor: Allen R. Grahn, Salt Lake City, Utah

[73] Assignee: Bonneville Scientific Incorporated, Salt Lake City, Utah

[21] Appl. No.: 504,224

[22] Filed: Jul. 19, 1995

Related U.S. Application Data

[63] Continuation-in-part of Ser. No. 329,465, Oct. 26, 1994, Pat. No. 5,553,500.
[51] Int. Cl.$^6$ .................................. G01L 5/16; G01H 5/00
[52] U.S. Cl. ......................... 73/628; 73/652; 73/862.043; 73/862.046; 73/862.541; 73/862.637
[58] Field of Search ............................... 73/627, 628, 644, 73/652, 862.041, 862.042, 862.043, 862.046, 862.05, 862.541, 862.637

[56] References Cited

U.S. PATENT DOCUMENTS

| 4,547,668 | 10/1985 | Tsikos . | |
|---|---|---|---|
| 4,599,908 | 7/1986 | Sheridan et al. . | |
| 4,704,909 | 11/1987 | Grahn et al. | 73/862.043 |
| 4,964,302 | 10/1990 | Grahn et al. | 73/862.046 |
| 4,998,441 | 3/1991 | Stuart | 73/862.043 |
| 5,209,126 | 5/1993 | Grahn | 73/862.046 |
| 5,295,399 | 3/1994 | Grant et al. | 73/862.043 |
| 5,341,687 | 8/1994 | Stan | 73/862.046 |

OTHER PUBLICATIONS

Bauer, F., Piezoelectric and Pyroeletcric Polymers, *Polymers as Synthetic Metals Conference*, London, May 1983.
Begej, S., Finger–Shaped Tactile with Shear Force–Sensing Capability, NSF–88–50, *Abstracts of Phase I SBIR Awards, NSF*, 1988.
Cutkosky, M. R., et al., Skin Material for Robotic Fingers, *IEEE International Conference on Robotics and Automation*, Mar. 1987.
Grahn, A. R., et al., Six Component Robotic Force–Torque Sensor, *Final Report* 178347, 1987.

Hackwood, S., et al., A Torque–Sensitive Tactile Array for Robotics, *International Journal of Robotics Research*, vol. 2, No. 2, Summer 1983.
Hackwood, S., et al., A Torque–Sensitive Tactile Array for Robotics, *International journal of Robotics Research*, vol. 2, No. 2, Summer 1983.
Harmon, L. D., Robotic Taction for Industrial Assembly, *Report No. 1. Dept. of Biomed. Eng. Case Western Reserve Univ.*, Oct. 1982.
Howe, R. D., et al., Review of Robotic Tactile Sensing, to be published, 1989.
Jacobsen, S. C., et al., Tactile Sensing System Design Issues in Machine Manipulation, *IEEE Robot Conf. Proc.*, 1987.

(List continued on next page.)

Primary Examiner—Hezron E. Williams
Assistant Examiner—Rose M. Miller
Attorney, Agent, or Firm—Trask, Britt & Rossa

[57] ABSTRACT

A triaxial force sensor using a hemispherical target supported by a compliant element such as a spring or an elastomer supported by a rigid support member. The sensor includes a plurality of ultrasonic transducers disposed in a plane at equal intervals about the target and vertically and laterally offset from the target. The transducers are oriented at an oblique angle to the plane, and aimed at the target in its rest position. The target is displaced by sufficient force applied to elastically deform the compliant element, which displacement alters the transit times of ultrasonic signals from the transducers which are reflected from the target. If at least three sensor units are employed non-colinearly, the six force-torque components, $F_x$, $F_y$, $F_z$, $M_x$, $M_y$, $M_z$, can be determined from the pulse transit times, the speed-of-sound in the medium or media between the transducers and the target, the deformation response of the compliant element, and the known geometry and spacing of the transducers. Pairs of transducers may be rotationally offset from each other to determine different force-torque components. A plurality of sensors as described may be employed together in a multi-sensor array. An alternative embodiment employing both the amplitude and the transit time of an ultrasonic pulse is also disclosed.

37 Claims, 13 Drawing Sheets

OTHER PUBLICATIONS

Nicholls, H. R., et al., A Survey of Robot Tactile Sensing Technology, *International Journal of Robotics Research*, vol. 8, No. 3, Jun. 1989.

Siegel, D. M., et al, A Capacitive Based Tactile Sensor, *SPIE vol. 579 Intelligent Robots and Computer Vision*, 1985.

Siegel, D. M., et al., Contact Sensors for Dexterous Robotic Hands, MS thesis, MIT, 1986.

Sinden, F. W., et al., A Planar Capacitive Force Sensor with Six Degrees of Freedom, *IEEE Robot Conf Proc.*, 1986.

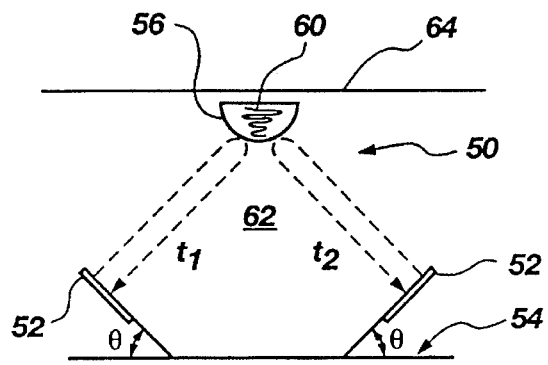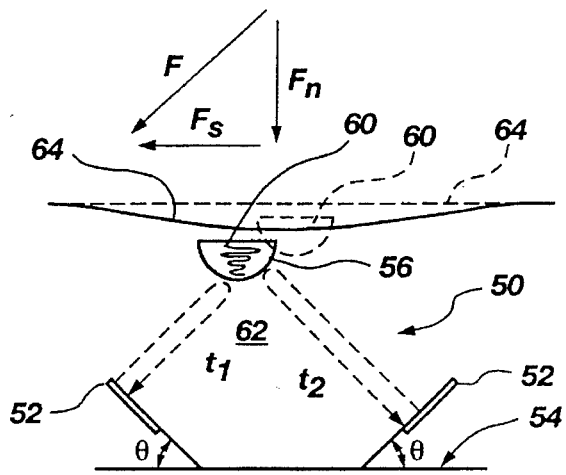
Fig. 1A                     Fig. 1B
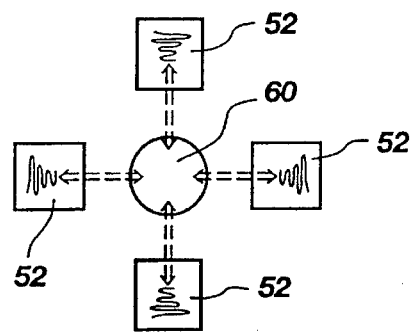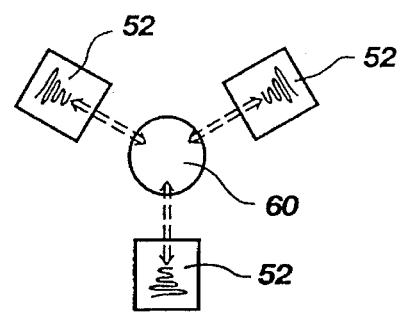
Fig. 2                      Fig. 3
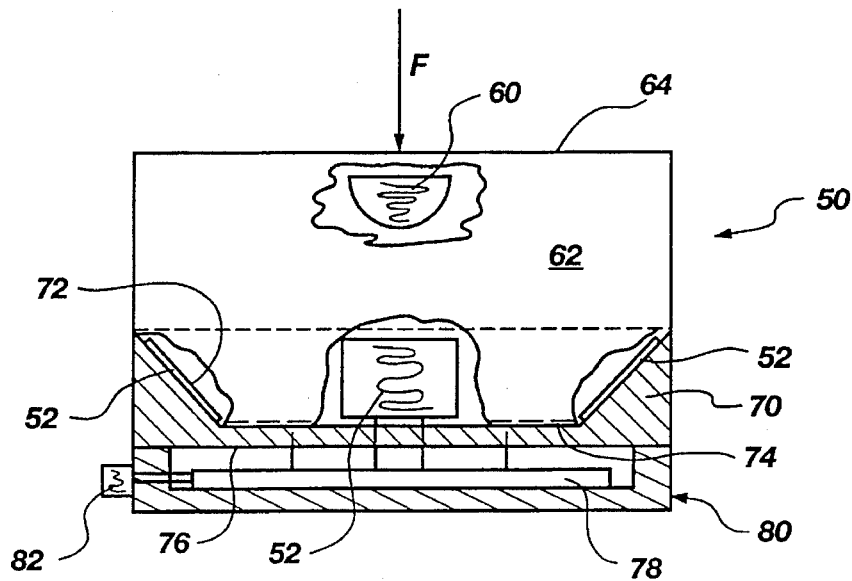
Fig. 4

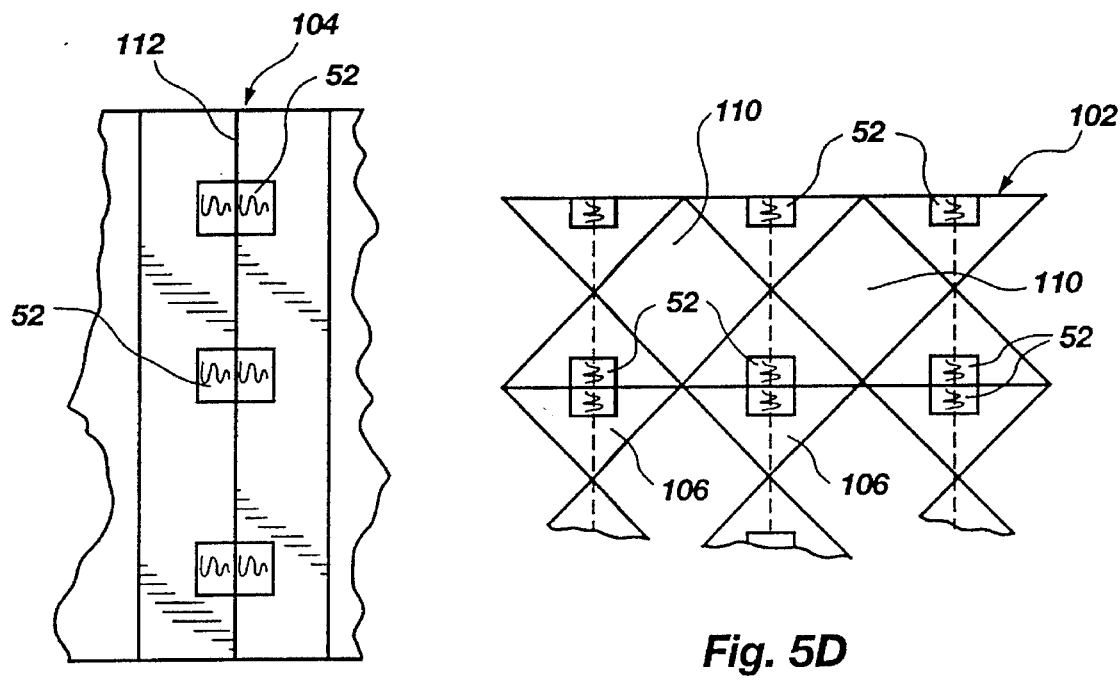
Fig. 5C
Fig. 5D
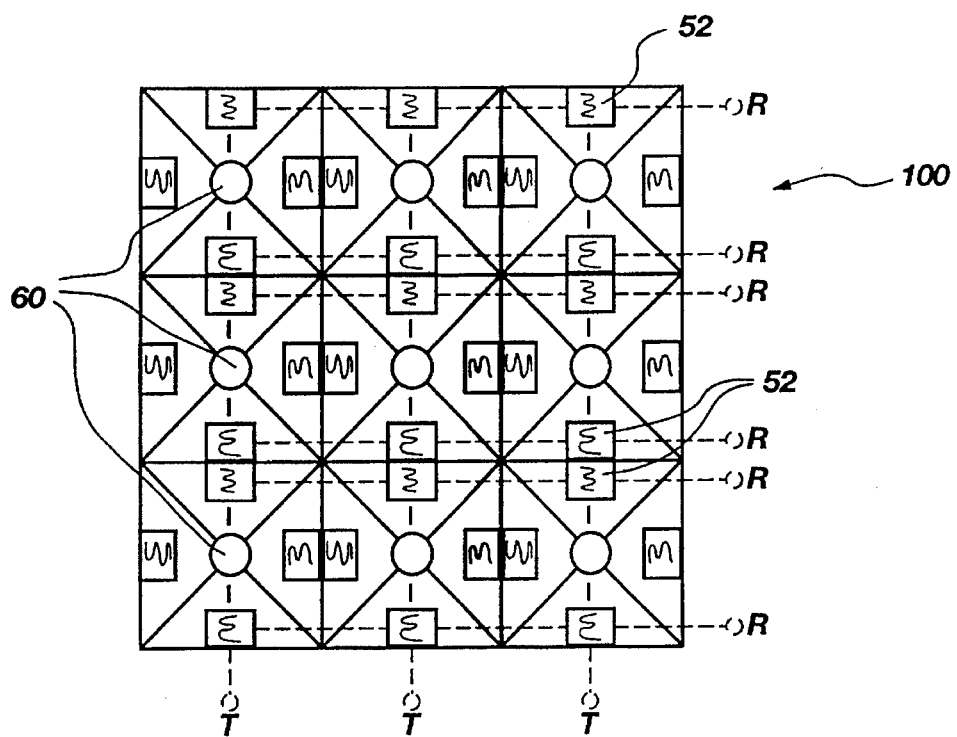
Fig. 6

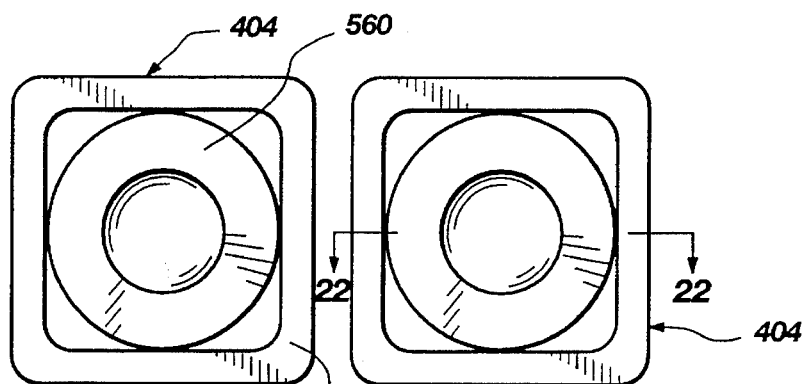
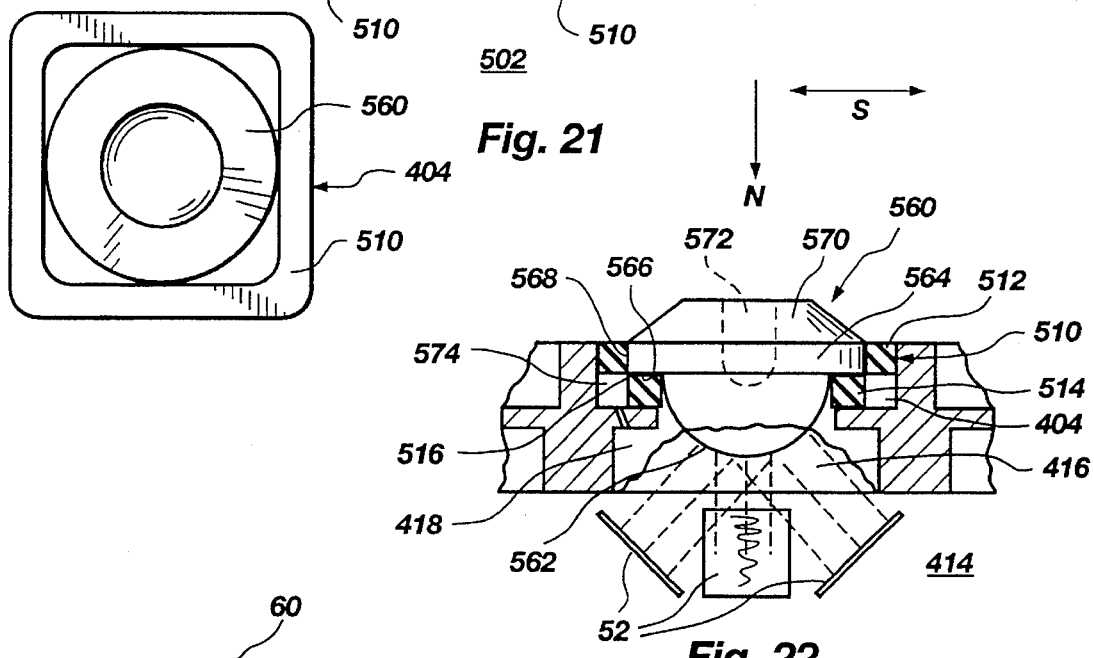
Fig. 21
Fig. 22
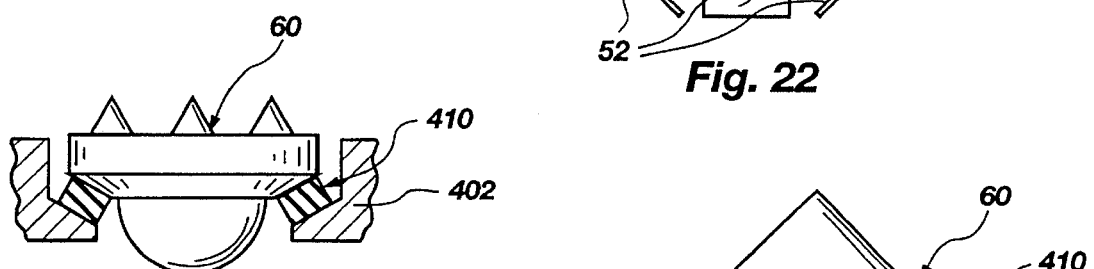
Fig. 23
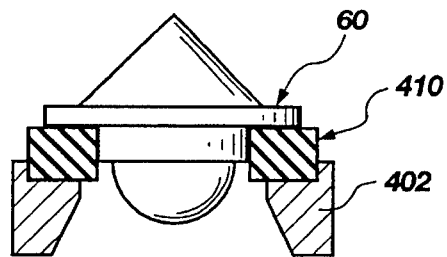
Fig. 24
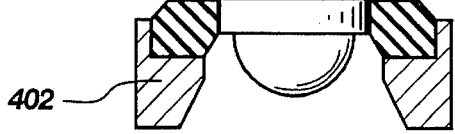
Fig. 25

TRIAXIAL NORMAL AND SHEAR FORCE SENSOR

This patent application is a continuation-in-part of patent application Ser. No. 08/329,465 filed Oct. 6, 1994, now U.S. Pat. No. 5,553,300, issued Sep. 10, 1996.

BACKGROUND OF THE INVENTION

1. Field of the Invention.

The present invention relates generally to force sensors, and more specifically to an ultrasonic sensor for the measurement of normal and shear forces.

2. State of the Art.

With rare exception, tactile or contact-type sensors in the art respond to normal forces only. From the measurement of normal force distribution, three ($F_z$, $M_x$, $M_y$) of the six force-torque components ($F_x$, $F_y$, $F_z$, $M_x$, $M_y$, $M_z$) can be computed. These three components are the normal force and the two orthogonal torques in the plane of the sensor. Normal-force sensing is adequate for tasks involving object or feature identification, determining object location with respect to the sensor, and under some circumstances, estimating impending slip from the normal force and knowledge of the coefficient of friction between the object and the sensor surface.

However, for certain applications, such a limited sensing capability is inadequate. Examples of such applications include, without limitation, grasping and manipulation by a robot hand; measurement of forces generated by an object such as a tire, shoe, boot or ski moving over the sensor; determination of pressure points, forces and movements of bodily extremities with respect to footwear such as athletic shoes, boots, and ski boots as well as sporting (golf clubs, tennis rackets, baseball bats) and industrial (hand tools, grips for electrically-powered tools) implements; determination of balance and gait analysis for athletic training and medical treatment and rehabilitation; use in a joystick, cursor control or other position-dependent control devices; and for accelerometers.

There have been several attempts to develop arrays of triaxial force sensors or full six-axis tactile sensors. For example, tactile array elements have been composed of magnetic dipoles embedded in an elastomer, the position and orientation of which were detected by magneto-resistive sensors. However, only one- or two-element sensors have been fabricated to prove feasibility of the concept. Another approach has employed sensors using emitters (charge or magnetic) embedded in a compliant layer. Emitter position is measured by an array of field-effect transistors or Hall-effect devices fabricated on a silicon substrate. Prototype sensors of this design were found to be highly sensitive to external fields.

A capacitance-based approach has also been attempted, but implemented only with respect to normal-force sensing. An existing, optically-based tactile sensor may have been modified to incorporate shear sensing capabilities. Presumably, the technique being investigated is the position monitoring of optical targets embedded in a substrate. However, such a design does not lend itself to incorporation into necessarily compact sensors as used in robot end-effectors, due, among other consideration, to the presence of a relatively large, stiff bundle of optical fibers exiting the sensor.

A miniature force-torque sensor has been developed by the assignee of the present invention. This sensor was intended for mounting on the gripping surfaces of robot end-effectors. The sensor consists of an elastomeric spring element joining two rigid parallel plates, one of which is mounted to the end-effector. Ultrasonic pulse-echo ranging through the elastomer is used to detect free movements of one plate relative to the other. The sensor is compliant, the degree thereof as well as the sensitivity and load range of the sensor being alterable by changing the elastomer composition. The six force-torque components may be calculated from the transit times and specifically times-of-flight (TOF) of a plurality of differently-aimed pulse-echo signals as one plate is deflected with respect to the other under application of force. A further description of the aforementioned sensor appears in U.S. Pat. No. 4,704,909, assigned to the assignee of the present invention, and incorporated herein by reference.

Other force sensors developed by the assignee of the present invention, which sensors employ pulse-echo ranging, are U.S. Pat. Nos. 4,964,302 and 5,209,126, assigned to the assignee of the present invention and incorporated herein by reference. The sensors disclosed in these two patents do not, however, have triaxial force component determination capability.

SUMMARY OF THE INVENTION

The sensor of the present invention provides a highly accurate, robust and relatively inexpensive sensor, in comparison to prior art sensors known to the inventors. In its preferred embodiments, the sensor employs transit time of reflected ultrasonic pulses to determine three force components. The sensor may be used singly, or in arrays incorporating a plurality of basic sensor units.

A preferred embodiment of the basic sensor unit of the present invention comprises a target suspended above laterally- and vertically-offset ultrasonic transducers, each having an emitting and receiving capability. The target is preferably of spherical or hemispherical shape; if the latter, the flat portion of the hemisphere is oriented parallel to the plane in which the transducers are located, with the arcuate portion of the hemisphere facing the plane. The transducers are aimed at the target and thus emit signals at an oblique angle to the transducer plane. The target is preferably embedded in a compliant material, such as an elastomer layer, which extends at least partially between the target and the transducers. Forces applied to the surface of the elastomer layer above the target distort the elastomer and may move the target both vertically and horizontally with respect to its original position. Target position is measured by ultrasonic echo-ranging; that is, one measures transit time of the obliquely-oriented ultrasonic pulses which pass from each transducer through the elastomer, impinge upon the target and reflect back to that transducer. From the transit time measurement and knowledge of the speed-of-sound within the elastomer, the distance from the transducer to the target can be calculated. Since a plurality of transducers are disposed about and aimed at the target, target movement results in a plurality of different transit times, from which force components can be calculated using the known compressibility characteristics of the compliant layer. At least three, and preferably four, transducers are aimed at each target for triaxial force determination.

The basic sensor unit may also be employed in a joystick or cursor control device, or as an accelerometer. In the latter case, a second group of transducers may be placed over the target in contraposition to the first set, if desired, for the contemplated application.

If desired, a plurality of basic sensor units may be arranged in a planar sensor array, the term "planar" being used herein to denote not only a sheet-like array extending in a linear plane, but also such an array which is concave, convex, or otherwise arcuate or non-linear in configuration, as required by the particular application.

Sensor accuracy may be enhanced with minimum time skew by pulsing each transducer in rapid succession before the echo of the preceding pulse has returned to the transducer. The time lag or difference of the second and successive pulses in a pulse burst after the first pulse is subtracted from the transit time of that pulse. The resulting, lag-compensated transit times of the pulses in a burst are then averaged.

If an array is formed, the scan rate to effect continuous scanning of all targets in the sensor array may be enhanced by rapidly pulsing transducer columns in succession before the pulses from the previously-pulsed columns have reflected and returned to the transducers of those columns.

An alternative transit time measurement technique, in lieu of pulsing an ultrasonic signal toward the target, is to generate a continuous oscillatory signal or several cycles of continuous signal and to measure the phase shift between the outgoing and returning (reflected) signal. Hence, the term "transit time measurement" as used herein is intended to encompass such measurement by phase shift determination.

In development of the invention in the form of an array of basic sensor units, it has been determined that particular structural features of an array may present advantages in terms of the ability of an array to withstand relatively large forces and to measure such forces in terms of normal and shear force components in an accurate manner, as well as ease of initial fabrication and repair or replacement of array components. Such features include the use of a rigid planar support member, such as a metal plate, to support a plurality of targets (such as in a 4×4 or 8×8 target array), each target being associated with an individual biasing element and each target/biasing element combination being disposed in an individual aperture extending through the support member, which overlies the transducers of the array and aligns each target with its associated transducers. Another advantageous feature for fabrication of an array is the horizontal or planar placement of the transducers, aimed upwardly and perpendicular to the transducer plane, in combination with the use of acoustically refractive elements or "prisms" to reorient the ultrasonic waves of the transducers of each basic sensor unit at desired oblique angles toward the target. Such a design greatly simplifies construction of the array, and may result in a sturdier structure than is possible with some other embodiments of the invention. Reflectors may also be employed in lieu of refractive elements. Further, directly-aimed transducers may be employed in combination with refractively- or reflectively-aimed transducers (or the latter two with each other) in an array or in a basic sensor unit, to accommodate physical design constraints or a particular sensor or array topography.

BRIEF DESCRIPTION OF THE DRAWINGS

FIGS. 1A and 1B are schematic side elevations of an illustrative transducer and target arrangement for two-dimensional monitoring of target position;

FIG. 2 is a schematic top elevation of a target and four-transducer configuration as may be employed in a basic sensor unit;

FIG. 3 is a schematic top elevation of a target and three-transducer configuration as may be employed in a basic sensor unit;

FIG. 4 is a partial section side elevation of a preferred configuration for a four-transducer basic sensor unit;

FIG. 5C is a top elevation of a ridgeline of the lower substrate of the array, and FIG. 5D is a top elevation of a portion of the segmented upper substrate of the array;

FIG. 6 is a schematic top elevation of the single-level, multi-sensor array of FIG. 5;

FIG. 21 is a top elevation of three sensor unit targets supported by biasing elements in a rigid support member of a multi-sensor array;

FIG. 22 is a partial sectional side elevation of sa preferred target and biasing element configuration suitable for use with a rigid support member in a single- or multi-sensor array;

FIGS. 23–25 are partial sectional side elevations of alternative target, biasing element and support member configurations according to the present invention;

DETAILED DESCRIPTION OF THE PREFERRED EMBODIMENTS

Figure 5:
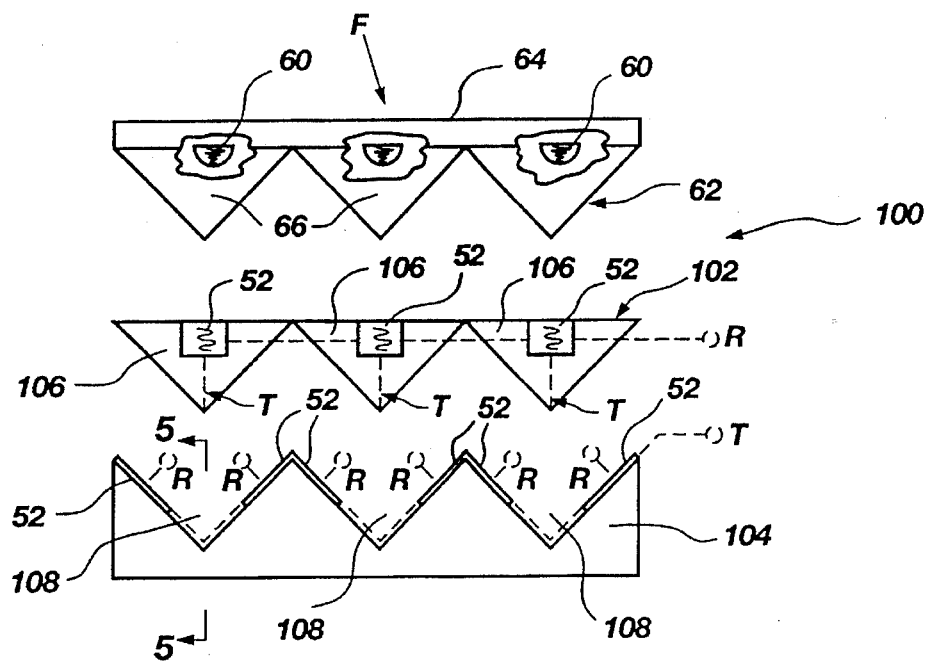
FIG. 5 is a schematic exploded side elevation of a preferred configuration for a single-level, multi-sensor array.

The force measuring technique for the sensor of the present invention is, in its simplest form, based upon ultrasonic pulse-echo ranging between a movable target and a transducer, although, as noted above, phase-shift measurement of an oscillatory signal may also be employed to determine signal transit time. The target is embedded in a deformable medium having known sound-transmission attributes, the medium extending between the target and the transducer. It is currently preferred that this deformable medium comprise an elastomer, and for purposes of convenience, the term "elastomer" will be employed in this discussion, although it will be understood that other materials, such as gels, rubber compounds, plastics, liquid-filled bags or balloons, etc., may be employed. Alternatively, a spring or springs such as coil, leaf, belleville or other spring configuration supporting a target may be employed in combination with a sound-transmitting medium to convey the ultrasonic signals. The target moves when the supporting medium is distorted or compressed by sufficient force. The distance between the target and the transducer is determined from the time it takes an ultrasonic signal to traverse the intervening medium and return. From this time interval measurement, hereinafter "transit time", knowledge of the speed-of-sound in the medium and the medium's modulus (i.e., the stress required to produce a particular degree of compression), the forces compressing the medium can be calculated.

Two basic principles are involved in pulse-echo distance measurement. First, the speed-of-sound, c, in the medium (elastomer) is known so that its thickness between the target and the transducer can be determined from the two-way transit time, t, of the pulse, by:

$$d = \frac{1}{2} ct \quad (1)$$

The second principle is that the interface between the target and the elastomer must reflect the pulse. Therefore, it is imperative that the target have an acoustic impedance which differs significantly from that of the elastomer.

The time required for an ultrasonic pulse to make a round trip between the transducer and the target is given by equation (1) above. For 3 mm of silicon rubber, the time of flight (transit time) of the pulse is about 6 microseconds. Therefore, if the expected maximum force compresses the rubber to 60% of its original thickness (1.2 mm compression) and it is required to resolve this force to one part in 200 (corresponding to a distance resolution of 6 microns), then the ultrasonic pulse transit time must be resolved to within 12 ns.

Polyvinylidene Fluoride (PVDF) is preferably used for the transducer materials in the sensor of the invention. The material has a low mechanical Q, low acoustic cross coupling between adjacent array elements, and simplifies array fabrication. PVDF is a thin-film polymer material which is demonstrated to be five to ten times more piezoelectric than crystalline quartz when stretched and poled. Other polymers which offer a piezoelectric capability may also be employed. It should be understood, however, that still other transducer materials, such as ceramics, may be used in appropriate circumstances such as in high-temperature environments.

A great degree of freedom is available in the choice of an appropriate elastomer for target support and signal transmission. The primary function of the elastomer is to act as a linear spring. Stated another way, the elastomer compresses in direct proportion to the amount of force applied. Ideally, the elastomer's force versus compression characteristics should be linear so that a simple proportionality constant can be used for force or pressure calculations.

The use of an elastomer-embedded target provides a number of benefits. For example, the exposed surface of the elastomer layer containing the target can sustain limited wear and damage without degradation of sensor performance. In addition, the elastomer layer above the reflectors may be made so that it can be replaced when it becomes damaged or contaminated. The exposed surface can be easily textured to aid in grasping or to reduce the normally high coefficient of friction (if rubber is used) to prevent sticking. Finally, sludge, mud or other contaminants on the sensor pad surface, or the manipulation of rubber objects, would not affect sensor performance.

FIGS. 1A and 1B depict a simplified transducer and target arrangement 50 according to the present invention for determining target position in two dimensions. Ultrasonic transducers 52, located in a common plane 54, are aimed at the arcuate surface 56 of hemispherical target 60. Transducers 52 are both vertically and laterally offset from target 60, so that ultrasonic pulses travel to and from target 60 through medium 62, typically an elastomer, at an oblique angle. With this configuration, the normal force and one of two shear-force components can be measured. The sum of the transit times from the transducers, $t_1 + t_2$, is proportional to the normal force component, $F_z$. The difference in transit times, $t_2 - t_1$, is proportional to the shear force component, $F_x$ or $F_y$.

The proportionality constants inferred above depend upon the speed-of-sound in the compliant, acoustically transparent medium 62 located between the transducers 52 and the target 60 (in order to convert the time interval measurement into distance), the appropriate elastomer stiffness constant, the geometry describing the positions of the transducers and target, and target geometry.

As shown in FIG. 1, when no force or pressure is applied to the contact surface 64 of the compliant medium (elastomer) in which the target is embedded, the transit times $t_1$ and $t_2$ are equal. When a force F is applied to contact surface 64, the medium 62 distorts and compresses in the direction of the force vector, and target 60 is displaced in proportion to the level of force F applied. Transit times $t_1$ and $t_2$ then differ, and from this difference the target location may be calculated. For measuring a second shear force component, another pair of transducers 52, as shown in FIG. 2, may be positioned at right angles to the first pair. If desired, only three transducers 52, as shown in FIG. 3, may be disposed about a target 60 at 120° intervals for measurement of the three force components. Such an arrangement minimizes the number of transducers required, but may not be desirable, as it complicates the otherwise straightforward mathematics involved in calculating the target position, and it is difficult to fabricate multi-sensor arrays using this arrangement.

The angled ultrasonic pulses (i.e., angle $\Theta$ in FIGS. 1A and 1B) can be obtained by mounting the transducer material on angled facets, mounting the transducer material on a flat surface and using reflectors to reflect the pulses at the desired angle, or mounting the transducer material on a flat surface and using wedges of a suitable material like prisms to refract the pulses at the desired angle. The first alternative is preferred, due to the bulk added to the sensor by the other two alternatives, and, in the third alternative, the severe constraints placed on the acoustic properties of the refracting wedge material. For arrays with a large number of basic sensor units, the PVDF transducer material for a large number of transducers should be installed as a single sheet in a single operation rather than employing single, discrete transducer elements or strips of such elements. This approach renders multi-sensor arrays much more economical, as well as ensuring more accurate transducer placement.

Figure 12:
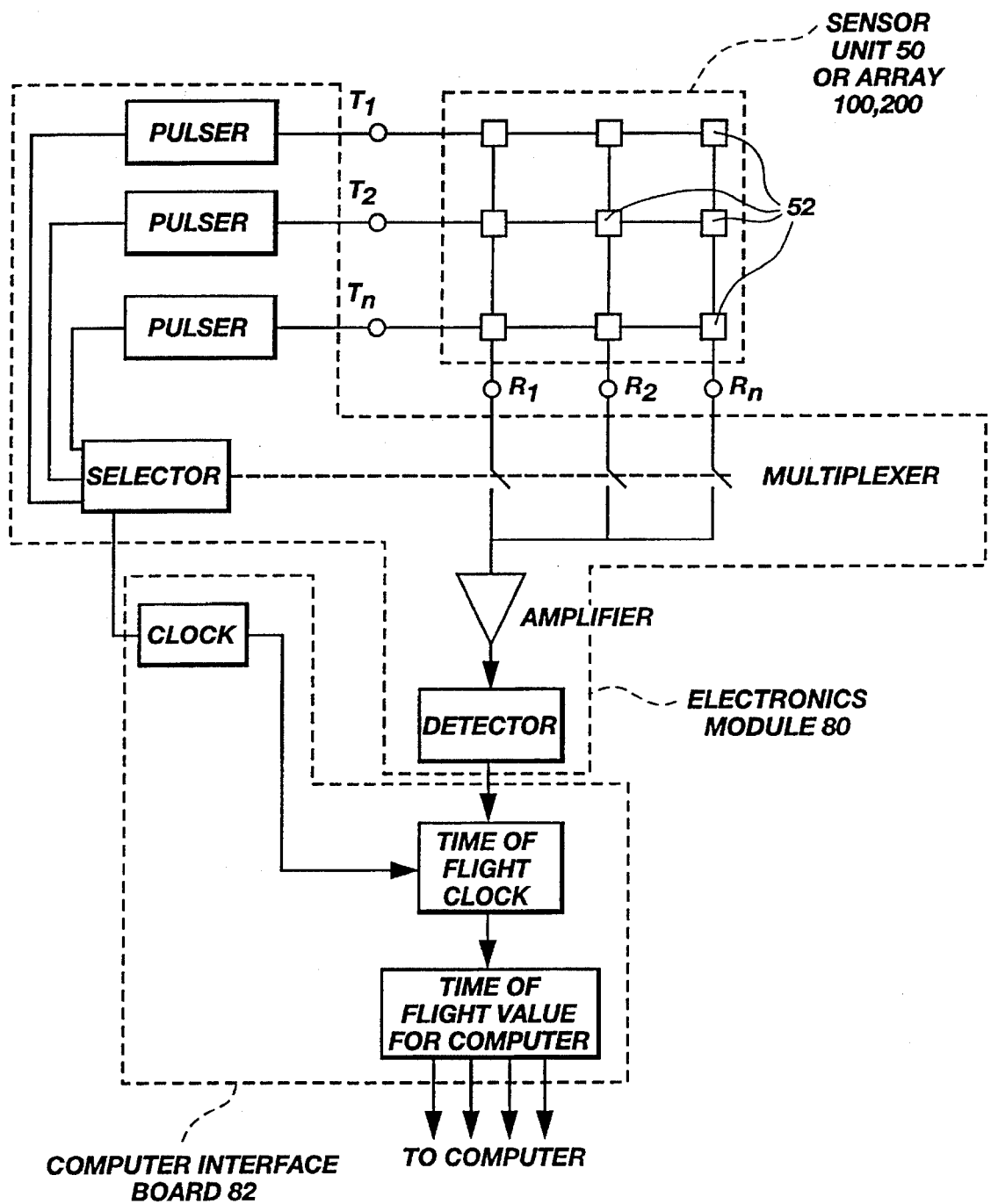
FIG. 12 is a schematic of the processing circuitry employed to convert pulse transit times from transducers aimed at a target into the actual target position.

FIG. 4 depicts a preferred physical configuration for a four-transducer basic sensor unit 50 in accordance with the present invention. The four PVDF film transducers are mounted to a substrate 70 with an inner wall 72 set at a 45° angle. Target 60 is embedded in a compliant medium 62 which extends between the target 60 and the transducers, filling the void therebetween. The upper surface 64 of medium 62 provides a contact surface for application of a force, F. Wires or printed conductors, shown in broken lines at 74 (preferably the latter, and molded into or onto substrate 70 at the time of its fabrication) extend through substrate 70 to the lower surface 76 thereof, where they communicate with conductors of the electronics 78 of electronics module 80 disposed underneath substrate 70. Electronics module 80 then communicates with a host processing unit such as a personal computer (PC) via connector 82 and a suitable interface board. FIG. 12 depicts a schematic of the circuitry of the electronics module 80 and interface board with a sensor unit of array 100, wherein the transducers 52 are selected and pulsed, the ultrasonic echo signals are amplified and detected, and the corresponding transit times are measured. The detected pulse transit times are converted to force component values by the PC using the known speed-of-sound and compliancy characteristics of the medium supporting the target 60.

FIGS. 5, 5A–5D and 6 depict a preferred embodiment of a single-level, multi-sensor array 100 of the present invention. For the sake of clarity, reference numerals previously employed are used again to identify the same elements. In array 100, a plurality of hemispherical targets 60 (nine in this instance, for exemplary purposes only, and not by way of limitation) are disposed above transducers 52, each target 60 having four transducers 52 aimed at it, preferably from a common distance and angle. If a wide angle (e.g., 25° to the sensor plane) is employed, the sensor unit may be made thinner, but shear force sensing capability is somewhat diminished. If a closer angle is employed (e.g., 60° to the sensor plane), greater shear force sensitivity results. Targets 60 are embedded in a compliant medium 62, which provides a contact surface 64 for the application of a force, F. A first plurality of rows of transducers 52 are carded by perforated substrate 102, and a second plurality of rows of transducers 52 running at a 90° angle to the first plurality are carded by ridged substrate 104.

As can be seen by viewing FIGS. 5, 5A, 5C and 5D together, segments 106 of perforated substrate 102 are received in valleys 108 of ridged substrate 104. When the two substrates are assembled, windows 110, the widest portions of which lie along ridgelines 112, provide transducers 52 of ridged substrate 104 with a clear field of fire at targets 60. Compliant layer 62, with targets 60 molded therein, includes protrusions 66 which are received in each recess flanked by four transducers 52 when perforated and ridged substrates 102 and 104, respectively, are assembled.

Figure 5A:
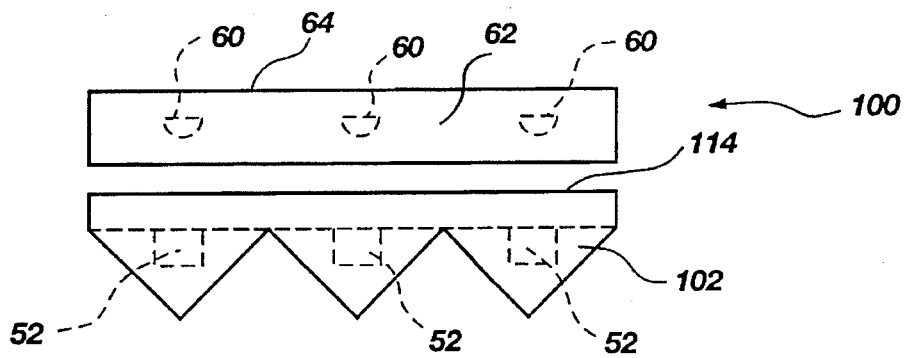
FIG. 5A is a depiction of an alternative layering arrangement for target placement and transducer protection.
Figure 5B:
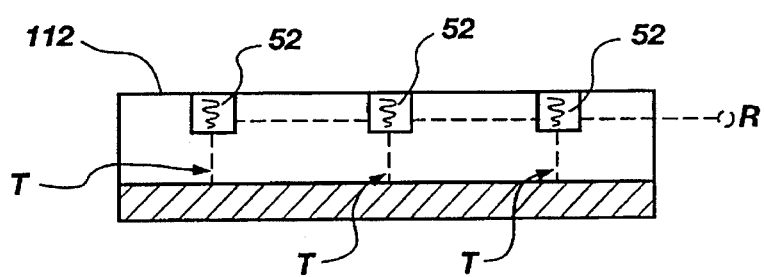
FIG. 5B is a section taken along fines 5—5 in FIG. 5.

As shown in FIG. 5A, targets 60 may be embedded in a separate compliant layer 62, which is easily removable and replaceable for repair purposes and to provide a ready means for altering the compliancy of the support for targets 60 to accommodate differing anticipated force ranges. In this case, substrate 102 is molded so as to have transducer 52 embedded therein as shown and to provide a continuous, planar upper support surface 114 for compliant layer 62. This arrangement also offers better protection for the transducers than the arrangement of FIG. 5.

As shown in FIGS. 5 and 6, transducers 52 are activated in columns by transmitting conductors T to emit ultrasonic pulses which are then reflected from targets 60 and received by the same transducers 52 from which they are emitted, the received signals being output from transducers 52 via receiving conductors R. This arrangement is depicted and described in more detail with respect to FIG. 8.

It will be readily understood that the medium extending between targets 60 and transducers 52 must be sufficiently acoustically transparent and nonrefractive for the ultrasonic pulses to travel therethrough without excessive attenuation and via a direct and consistent path. The term "medium" of course, is not limited to single-component mediums, but may comprise multiple layers. Unless the ultrasound signals contact the interface of two medium components at about 90°, it is desirable that the components' indices of refraction be substantially similar.

Figure 7A:
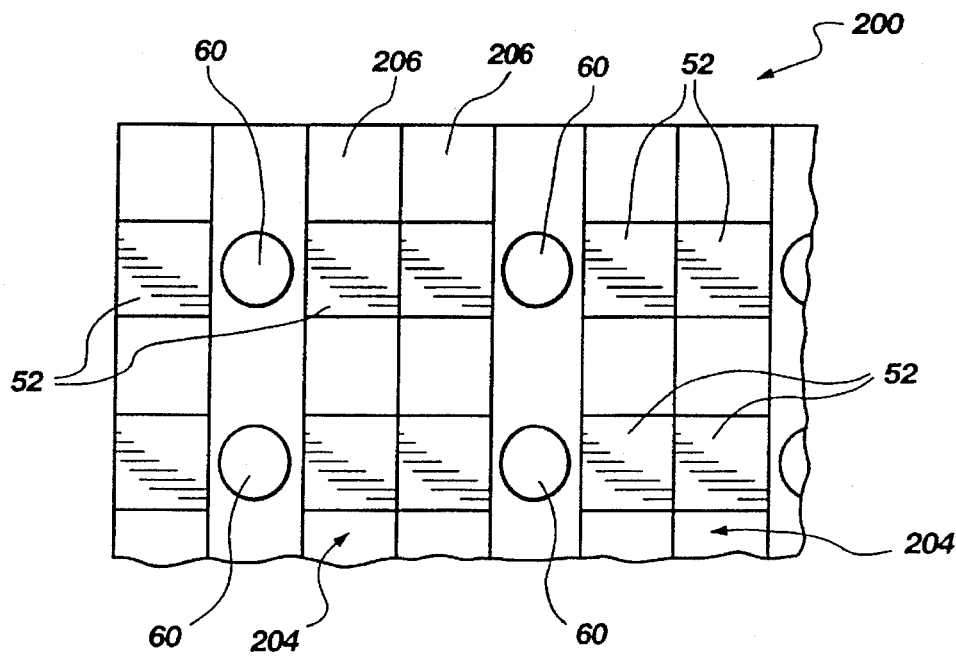
FIG. 7A is a schematic top elevation of an upper transducer level of an alternative multi-level, multi-sensor array embodiment of the invention.
Figure 7B:
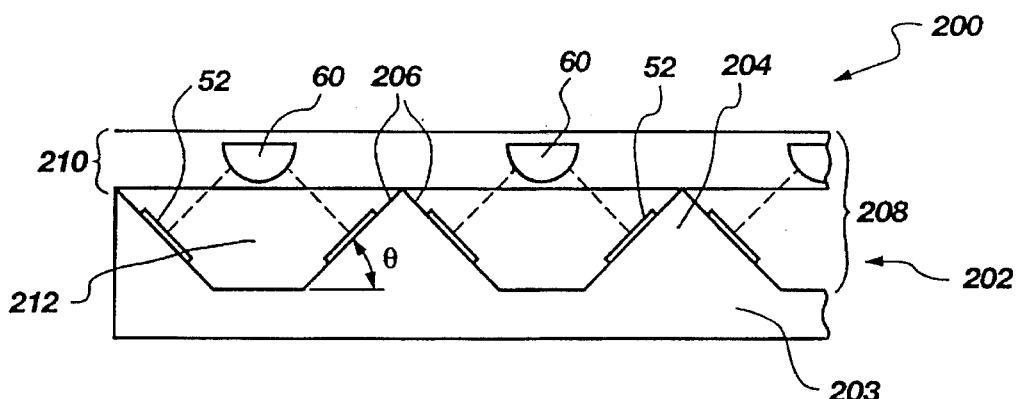
FIG. 7B is a schematic side elevation of the upper transducer level depicted in FIG. 7A.

An alternative multi-level, multi-sensor, array embodiment 200 of the invention is depicted in FIGS. 7A through 7D. Upper transducer level 202 includes an acoustically-transparent substrate 203 having a plurality of ridges 204 which, in three dimensions, would extend outwardly from the plane of the drawing, the ridges each having two sides 206 disposed at the same angle $\Theta$. PVDF transducers 52 are located at predetermined intervals along the ridges, as shown in FIG. 7A. Each of a plurality of targets 60 is located between a pair of transducers 52 aimed at that target. As shown in FIG. 7B, the targets are located "above" the transducers 52 in upper level 202, the term "above" being relevant only insofar as the drawing is concerned, it being understood that the sensors and sensor arrays of the present invention may be used in any orientation.

In one arrangement, the ridges 204 may project into the compliant, acoustically-transparent, nonrefractive elastomer layer 208 in which the targets 60 are embedded. It may be preferred for some applications to fully embed the ridges 204 and transducers 52 in one layer of elastomer or, alternatively, in a substantially noncompressible but acoustically transparent material layer 210, such as high durometer urethane compound to better protect the transducers, and to locate the targets in a separate compliant layer 212 thereabove. This also permits easy replacement of the targets and compliant upper layer 212 in the event of damage while the transducers remain unaffected.

Figure 7C:
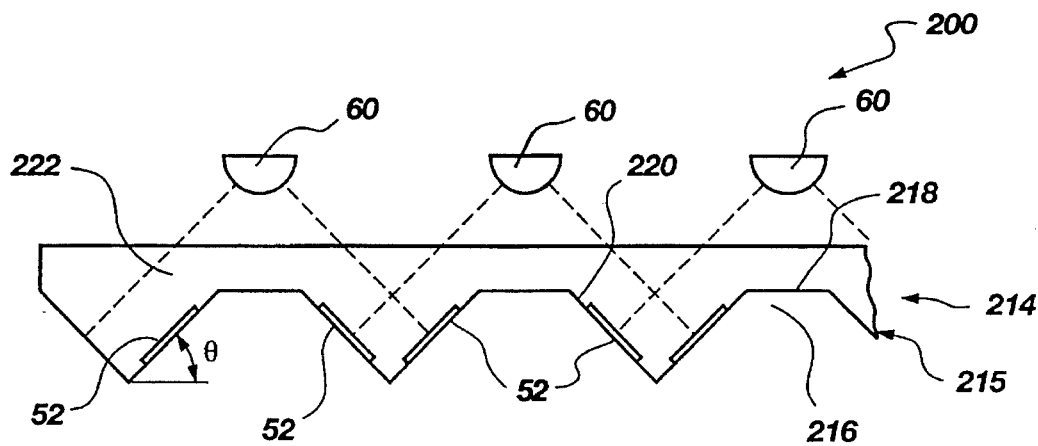
FIG. 7C is a schematic side elevation (rotated 90° about the vertical with respect to FIG. 7B) of a lower transducer level, of the multi-level multi-sensor array.

FIG. 7C depicts the lower level 214 of multi-sensor array 200. Lower level 214 is similar to upper level 202 and includes an acoustically-transparent substrate 215 including ridges 216, but ridges 216 in lower level 214 are truncated at their tops, providing flat upper surfaces 218 flanked by angled side surfaces 220 on which transducers 52 are mounted. Truncation of the ridges reduces the depth of the assembled sensor array 200, which is desirable for most applications. The transducers of lower level 214 transmit their pulses through the acoustically transparent material 222 overlying the lower level transducers 52, then through the upper substrate 203 and one or more higher layers such as 208, 210 and 212, depending upon the design employed, -to reach targets 60 and reflect therefrom back to the lower level transducers.

Figure 7D:
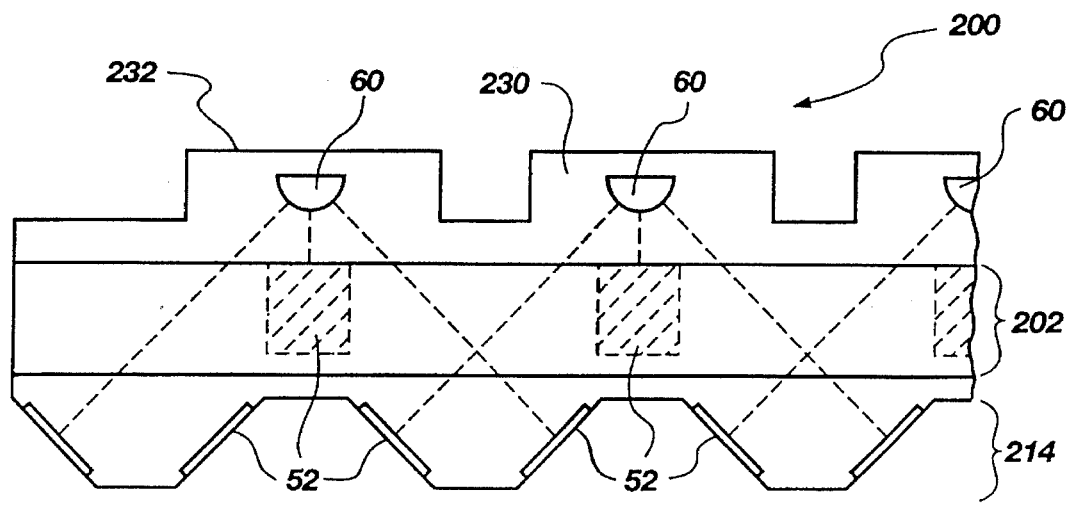
FIG. 7D is a schematic of the assembled multi-level, multi-sensor array.
Figure 11:
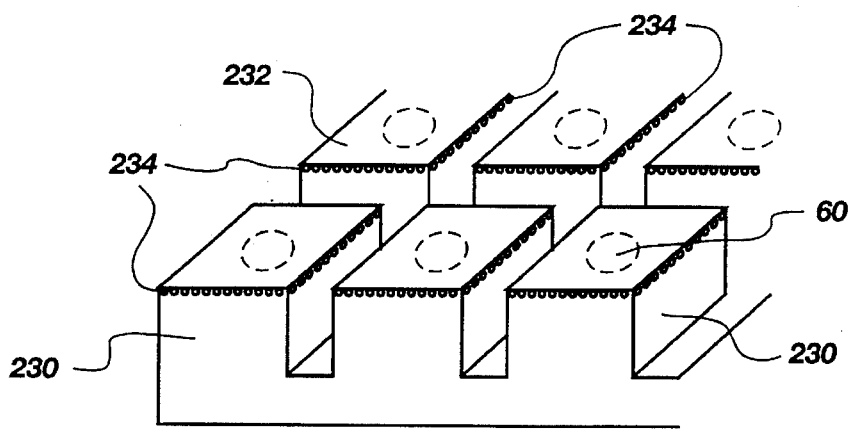
FIG. 11 is a perspective view of a plurality of basic sensor units incorporated in a multi-sensor array which includes a reinforced contact layer to accommodate high forces without degradation.

As shown in FIG. 7D, when assembled, sensor array 200 includes upper level 202 and lower level 214 at right or 90° angles, relative to the vertical. This rotational offset of the upper and lower levels 202 and 214 permits, as shown, the pulses from the transducers 52 of both upper and lower levels 202 and 214 to reach the targets 60 without interference. It is also noteworthy, again with reference to FIG. 7D, that the transducers 52 of lower level 214 are aimed at targets 60 which are farther laterally distant, permitting equal angles for transducer orientation in both levels. Finally, also as shown in FIG. 7D, it may be desirable to segment the upper elastomer layer containing the targets 60 into discrete blocks 230, each block being free to move relatively independently of the others. Such a configuration can reduce hysteresis and help prevent the embedded targets 60 from separating from the elastomer. Also, in some high-force applications, it may be desirable to reinforce the exposed elastomer pad surface 232 (see FIG. 11) with, for example, steel, Kevlar, nylon or other cord material 234 such as is employed in vehicle tires, or even a metal plate or non-woven mesh. It may also be desirable to coat or cover the pad surface 232 with a more wear-resistant material or one having a different coefficient of friction with respect to that of the element contemplated to apply force F to it, so as to enhance or reduce friction between the pad surface 232 and the contacting element.

With respect to the multi-layer embodiment 200, it again is important to emphasize that the material between the lower level of transducers 52 and the target 60 must be both sufficiently acoustically transparent and nonrefractive so as to avoid undue signal attenuation. In other words, the reflection coefficient for the interfaces between material 222 and substrate 203 and between the material 210 and the elastomer layer 212 should be close to zero. Stated another way, the acoustic impedance of the materials on either side of these interfaces should be approximately equal. Therefore, the product of material density times speed-of-sound needs to be about the same for both materials.

Urethane materials appear to be most promising for fulfillment of these requirements. Urethanes are tough, abrasion resistant and have high tear strength. They are also easy to bond to and readily pass ultrasonic waves. Furthermore, urethane compounds are available which can be formulated to have a wide range of harnesses, from approximately 15 Shore A to 75 Shore D durometer. In many applications, the first would be more than soft enough for the sensor pad or elastomer layer in which the targets 60 are embedded. The latter would be almost rigid and thus entirely strong enough for the substrate material and protective layers overlying the transducers mounted on the substrates. Since all compounds are urethanes, their product of density and speed-of-sound can be made relatively close. Of course, it is contemplated that other materials such as natural rubbers, silicone rubbers, neoprene, butyl rubbers, etc., may have equal utility for certain applications. Since the speed-of-sound through silicone rubbers is about ⅓ less than through urethanes, better resolution may be obtained via use of the former. In addition, softer silicone compounds than urethanes are currently available, making silicones more desirable for some applications.

It should also be noted that ultrasonic pulses from lower level transducers may pass through the PVDF layers of the upper level, as well as through the substrate material itself. This presents little difficulty, as the PVDF material is almost acoustically transparent for this application; its acoustic impedance is close to that of urethane. Furthermore, it is very thin, relative to the acoustic wavelength employed, and the metallization on the PVDF has little effect on attenuation since it is very thin.

Figure 8:
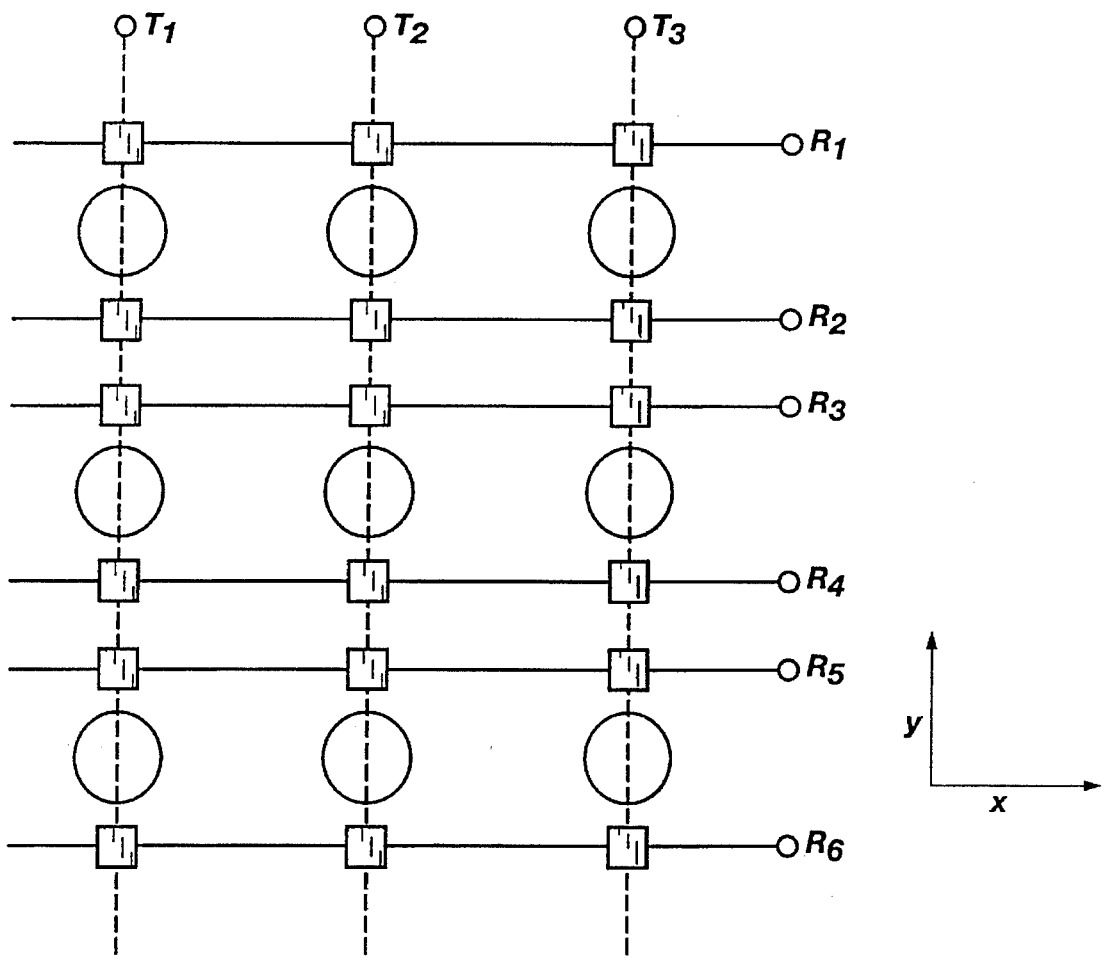
FIG. 8 is a wiring schematic of an array of transducers which may be employed with either the preferred or alternative embodiments of the multi-sensor array of the present invention.

FIG. 8 schematically depicts, from above, a wiring circuit which may be employed in either a single or multi-level, multi-sensor array for measuring the normal force $F_z$ and the $F_y$ shear force component. To prevent time skew in the $F_y$ measurement, one transmitting column such as $T_1$ would be pulsed and echoes would be received on the two receiving rows associated with the same site, such as $R_1$ and $R_2$, or $R_3$ and $R_4$, or $R_5$ and $R_6$. That is, there would be two parallel receiving/detecting channels associated with each target 60 associated with transmitting column $T_1$. Another, similar array structure contains the PVDF transducers and conductors for measuring $F_x$, the other structure being, as previously noted, rotated 90° with respect to the first.

Figure 9:
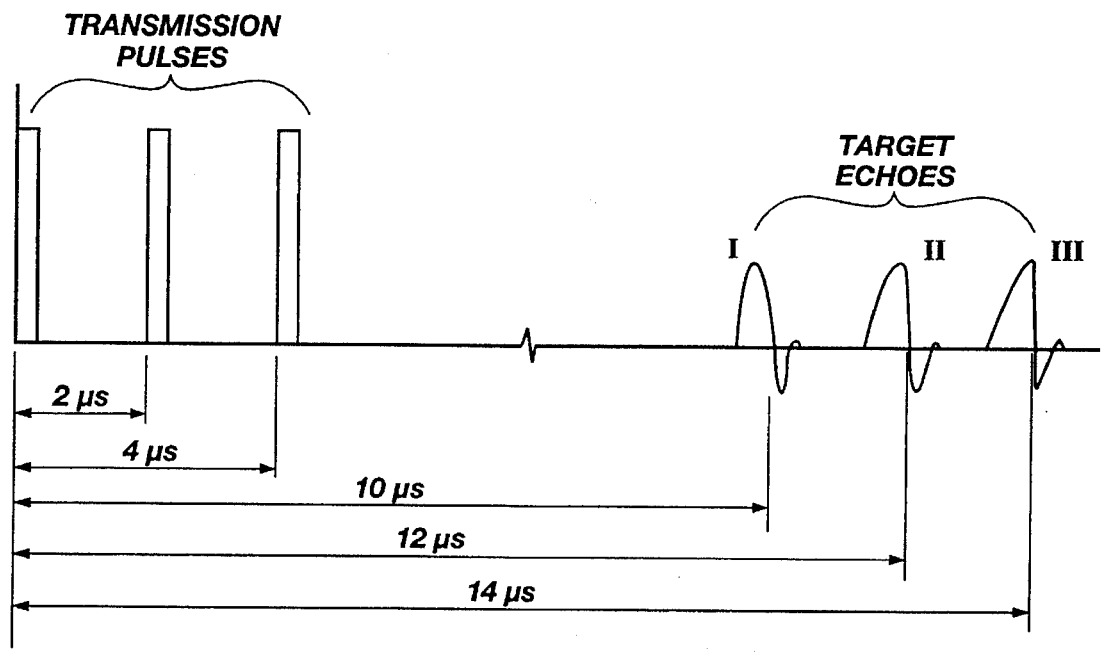
FIG. 9 is a timing schematic illustrating a technique of pulsing a transducer or column in a burst of closely time-spaced pulses to obtain an average value with minimum time skew.

FIG. 9 is an exemplary timing schematic for a technique permitting averaging of TOF measurements from and back to a single transducer 52 (at the intersection of one column and one row, as shown in FIG. 8), with minimal time skew. In the drawing figure, three excitation pulses are applied to the same transmitting column in rapid succession. The three echoes, I, II and II, produced by reflection of these pulses from a target 60 are detected in rapid succession. The pulses are emitted at 2 μs intervals, as shown. When echo II is detected, 2 μs is subtracted from its overall TOF value of 12 μs (12 μs–2 μs=10 μs). Similarly, 4 μs is subtracted from the overall TOF for echo III. The resulting TOF values for all three echoes are then averaged. Using such a "rapid-fire" pulsing technique, it takes only 14 μs, and not 30 μs, to make the three measurements. The above timing intervals and TOF figures are not meant to be accurate, but merely illustrative of the technique.

Figure 10:
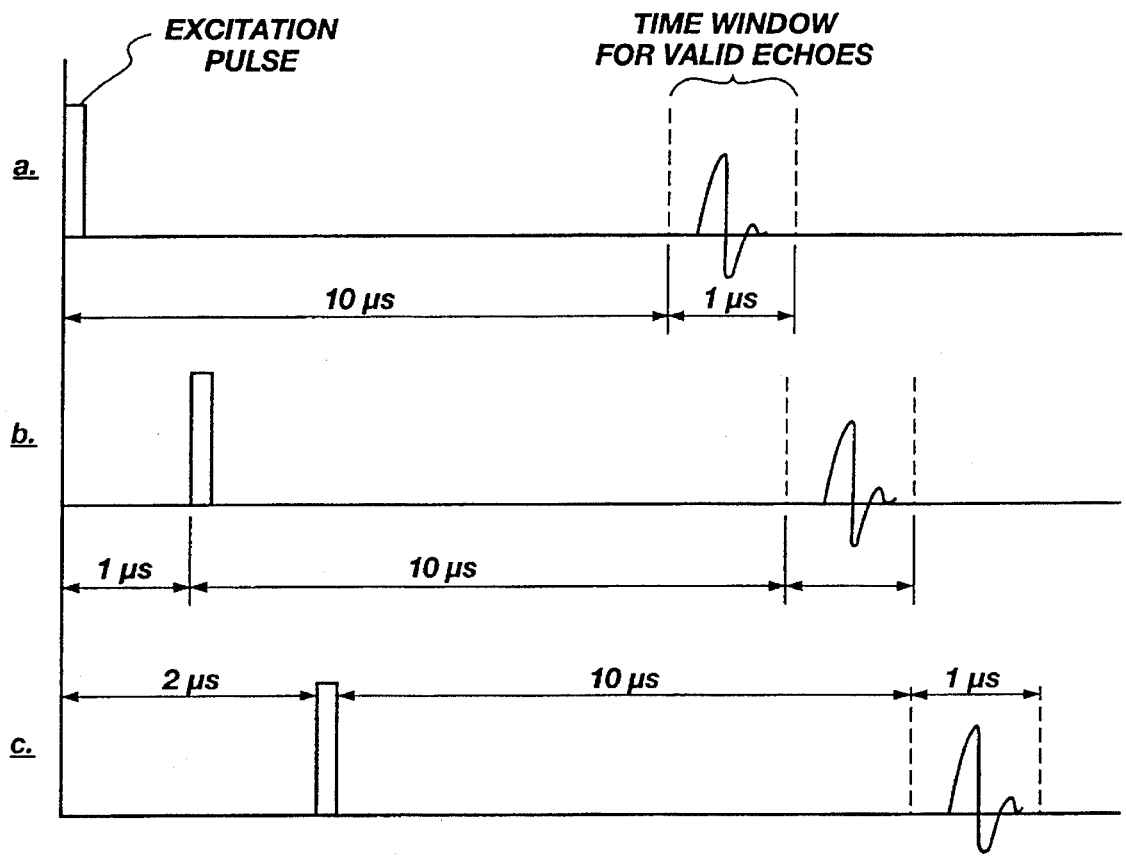
FIG. 10 is a timing schematic illustrating a technique of pulsing transducer columns in a multi-sensor array in rapid succession to effect continuous scanning of target positions.

FIG. 10 is an exemplary timing schematic for a technique of pulsing transmitting columns T (see FIG. 8) in rapid succession to increase the scan rate of the sensor array. Column a is pulsed, then b, then c, at 1 μs intervals. As shown, it would take only 13 μs to receive three echoes. The alternative of pulsing a column and waiting until the echo is detected before pulsing another column would take 11 μs per measurement, or 33 μs for detecting three echoes. Again, the stated timing intervals and TOF figures are not meant to be accurate, but merely illustrative of the technique.

To complete the sensor system according to the present invention, a few additional processing circuitry components are required. Specifically, an electronics module is employed to select and excite the array elements and multiplex the high-gain receiving amplifier. The module may be located at the sensor site or remotely therefrom. The module is also connected to a custom interface board in an IBM-compatible personal computer or other host proCessing unit. FIG. 12 is a schematic of the processing circuitry with the electronics module connected to a basic sensor unit or multi-sensor array, and to the interface board in the host processing unit.

Figure 13:
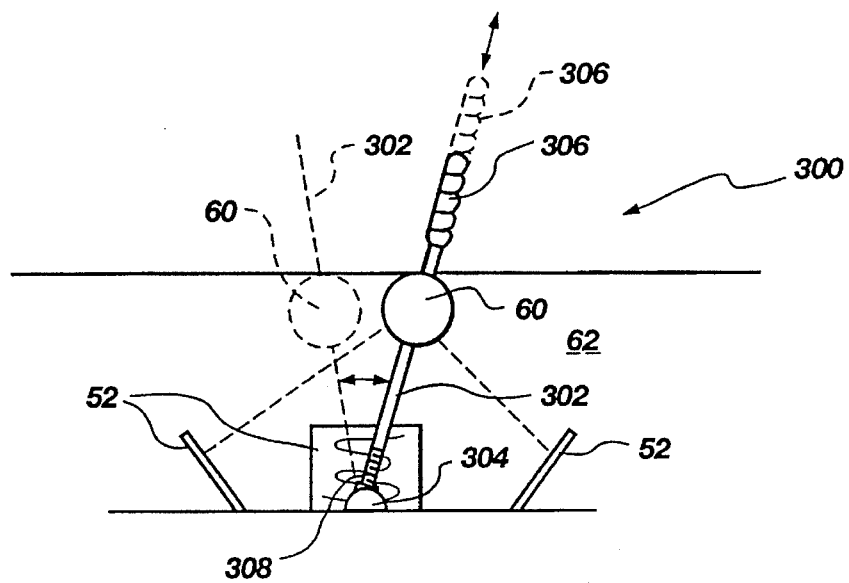
FIG. 13 is a schematic side elevation of the sensor unit of the present invention employed in a joystick.

FIG. 13 depicts a basic sensor unit 50 modified into a position-dependent control device 300 having four transducers 52 which has been modified by suspending target 60 from a joystick shaft 302 which is mounted to a universal or other flexible joint 304, providing the ability for a user to grasp a handle 306 at the upper end of the joystick shaft 302 and move it in any direction. Thus, the position of the joystick shaft 302 may easily be related to the transit times of the ultrasonic signals emanating from the transducers 52 through a sound-transmitting medium 62 interposed between target 60 and the transducers. This modification of the invention has ready applicability in joysticks for vehicle control, including aircraft, and for computer applications including cursor control and video games, as well as for commercial and industrial applications wherein the position of a control or sensing member is desired to be ascertained. Of course, the joystick shaft 302 may be spring-biased to return to a central or other desired position when no force is applied.

Figure 14A:
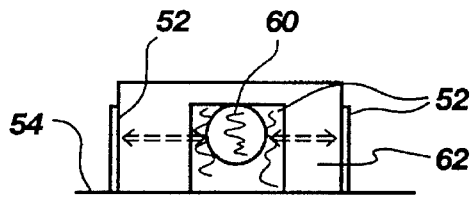
FIGS. 14A and 14B are schematics of the sensor unit of the present invention specifically adapted for use as an accelerometer.

FIG. 14A depicts the basic sensor unit 50 modified by positioning of the transducers 52 in a vertical orientation, with target 60 in the middle of the transducer group. Such an arrangement may be readily used as an accelerometer for forces in the plane 54 of the transducers 52, as movement and time of movement of target 60 in the surrounding compliant medium 62 responsive to acceleration or deceleration is easily measured. Such a modification of the invention may easily be used in a motor vehicle as a trigger for the deployment of airbags, particularly due to the recent development and emphasis on side-impact airbags by several manufacturers. Of course, if only fore-and-aft acceleration and deceleration are desired to be measured, a sensor unit employing only two transducers would suffice.

Figure 14B:
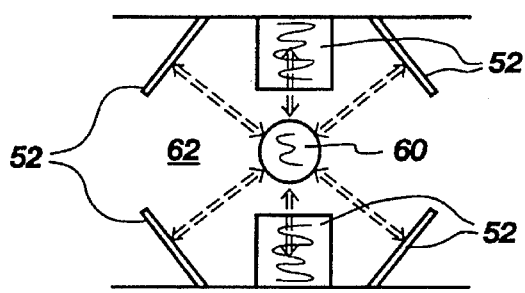

FIG. 14B depicts the basic sensor unit 50 augmented by the addition of four more transducers 52, arranged as the original four, but disposed above target 60. This modification of the invention is particularly suited for use as a triaxial accelerometer, such as are employed in aircraft and missile guidance systems, in test equipment for crash and other tests where acceleration and deceleration data is desired, and to control adjustable vehicle suspensions. Movement and time of movement of target 60 suspended within compliant medium 62 in any direction responsive to acceleration and deceleration forces is easily and accurately ascertained.

Figure 15:
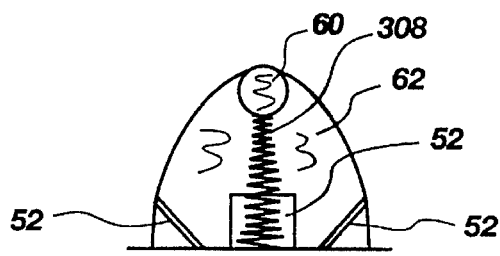
FIG. 15 is a schematic of a spring-supported target version of the invention.

FIG. 15 shows an embodiment of the sensor of the invention wherein target 60 is suspended on a spring 308 such as a coil spring, and a sound-transmitting liquid or gel medium 62 is interposed between transducers 52 and target 60. Of course, other spring types, such as belleville or leaf, might be employed, and it is contemplated that a plurality of springs might be used to support target 60 from below, from the side, and from above.

Following is a description of illustrative mathematics employed to determine the position (and therefore the forces) on a target 60 using the sensing geometry illustrated in FIGS. 1A and 1B, wherein one pair of transducers 52 is employed, the transducers being oriented at an exemplary angle $\Theta$ of 45° to the horizontal plane in which the transducers are located. For purposes of clarity, this geometry has been reproduced in much-simplified form in FIG. 16, with additional annotations as referred to below. The exact equations as set forth below would be straightforward to implement and would quickly run on a PC-class computer.

Figure 16:
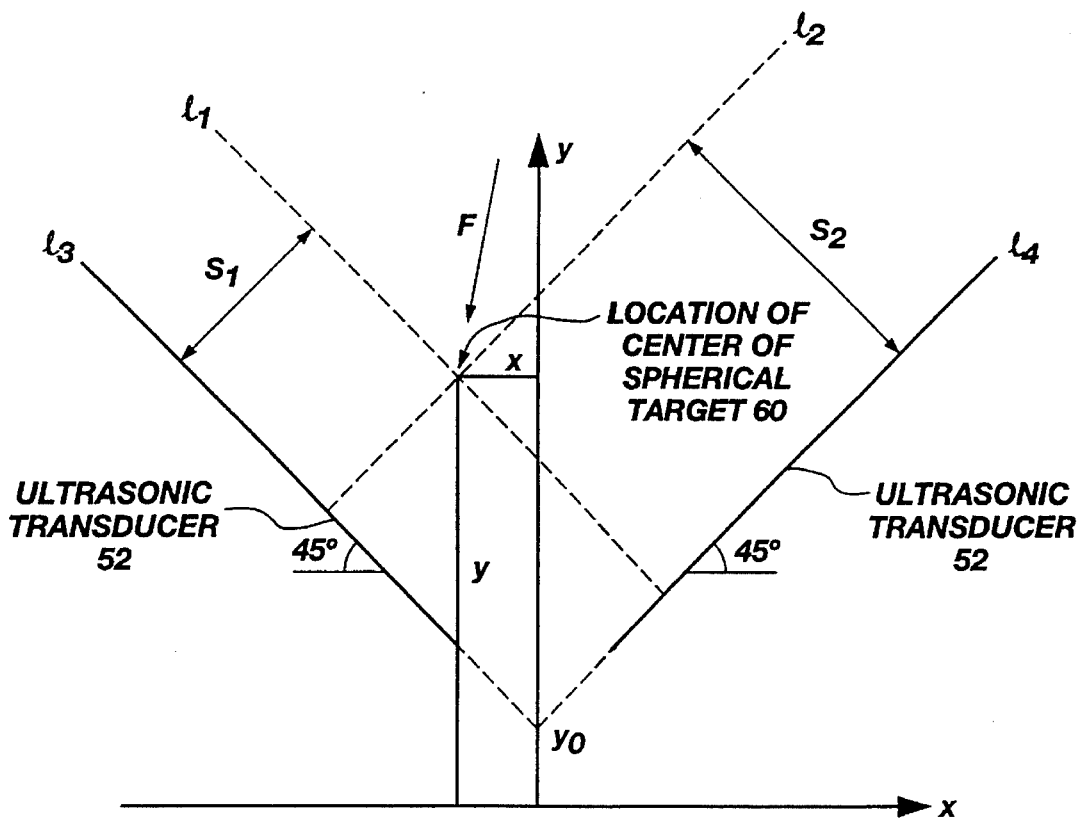
FIG. 16 is a simplified schematic of sensor geometry for mathematical purposes.

FIG. 16 shows the sensing geometry for one pair of ultrasonic transducers 52. These transducers would measure normal force and one component of shear force in the plane of the transducers. The equations for the other shear force component (at right angles to the first) would be similar. The approach taken is that the time-of-flight measurement (TOF) times the speed-of-sound÷2 plus the radius of the spherical target gives distances $S_1$ and $S_2$. Straight lines ($l_1$ and $l_2$) are drawn at these distances, parallel to the respective ultrasonic transducers ($l_3$ and $l_4$). These two lines ($l_1$ and $l_2$) intersect at a point (x, y) on the figure. This intersection point is the location of the diametrical center of the spherical or hemispherical target. The following should be noted:

1) The shear force is related to x, which is a function of $s_1 - s_2$.
2) The normal force is related to y, which is a function of $s_1 - s_2$.
3) The $$\frac{\sqrt{2}}{2}$$

factors are due to the transducers being oriented at 45°.

4) The actual forces are proportional to the change in TOF when no forces are applied vs when forces are applied (i.e., $t_{10} - t_1$ and $t_{20} - t_2$).
5) Adding the other two ultrasonic transducers does not affect the equations. It just adds two more equations of the same form.
6) Each pair of transducers gives a value for a shear force and the normal force. To improve accuracy, the two normal force values would be averaged.

Now:

For $l_2$: $y = mx + b$, $m = 1$
$y = x + b$
$b = y @ x = 0$
$b = y_0 + \sqrt{2}\ s_2$
$\therefore y = x + y_0 + \sqrt{2}\ s_2$ For $l_3$: $y = mx + b$, $m = -1$
$y = -x + b$
$y = b @ x = 0$
$\therefore b = y_0$
$\therefore y = -x + y_0$ For $l_4$: $y = mx + b$, $m = 1$
$y = x + b$
$y = b @ x = 0$
$\therefore b = y_0$
$\therefore y = x + y_0$ For $l_1$: $y = mx + b$, $m = -1$
$y = -x + b$
$b = y_0 + \sqrt{2}\ s_1$
$\therefore y = -x + y_0 + \sqrt{2}\ s_1$ Intersection of $l_1$ and $l_2$:

$y = -x + y_0 + \sqrt{2}\ s_1$
$y = x + y_0 + \sqrt{2}\ s_2$
$x + y_0 + \sqrt{2}\ s_2 = -x + y_0 + \sqrt{2}\ s_1$
$2x = \sqrt{2}\ (s_1 - s_2)$ when $s_1 = s_2$, $x = 0$ $\therefore x = \frac{\sqrt{2}}{2}\ (s_1 - s_2)$ $y = \frac{\sqrt{2}}{2}\ (s_1 - s_2) + y_0 + \sqrt{2}\ s_2$ Where c=the speed-of-sound in the elastomer $$= y_0 + \frac{\sqrt{2}}{2} s_1 + \frac{\sqrt{2}}{2} s_2$$

$$\therefore y = y_0 + \frac{\sqrt{2}}{2} (s_1 + s_2)$$

$$s_1 = (TOF)_1 \times \frac{c}{2} + \text{radius of target}$$

$$s_2 = (TOF)_2 \times \frac{c}{2} + \text{radius of target}$$

For forces, our calculations $\Delta x$ and $\Delta y$ $\therefore \Delta x = K_1 \{(t_{10}-t_1)-(t_{20}-t_2)\}$ = shear force $\Delta y = K_2 \{(t_{10}-t_1)+(t_{20}-t_2)\}$ = normal force Where $t_{10}$ is $(TOF)_1$, when no forces are applied, $t_{20}$ is $(TOF)_2$ when no forces are applied, $t_1$ and $t_2$ are $(TOF)_1$ and $(TOF)_2$, respectively, when a force F is applied and $K_1$ and $K_2$ are constants, which include the speed-of-sound in the elastomer, rubber stiffness, and the factor.

$$\frac{\sqrt{2}}{2}.$$

Using four transducers spaced at 90° intervals about a spherical or hemispherical target, all transducers being angled at 45° to the target, the mathematical equations giving the shear force in terms of TOF are quite simple. First of all, the x, y, z coordinates of the center of the reflector are:

$$x = \frac{\sqrt{2}}{2} (t_1 - t_3) c_1, \quad y = \frac{\sqrt{2}}{2} (t_2 - t_4) c_1 \text{ and}$$

$$z = z_0 + \frac{\sqrt{2}}{4} (t_1 + t_2 + t_3 + t_4) c$$

where $t_1$, $t_2$, $t_3$ and $t_4$ are the TOF's associated with pulses from each of the four transducers, and c is the speed-of-sound in the material disposed between the transducers and the target. Note, the above equations are only strictly true for a point target or reflector; for a real reflector target, a constant offset value has to be added. However, this offset cancels out of the equation when $\Delta x$ and $\Delta y$ are calculated. The forces corresponding to the change in position of the target are simply the change in coordinate value (from no force to force being applied to the sensor) time the appropriate rubber stiffness parameter (shear stiffness for $F_x$ and $F_y$, compressive stiffness for $F_z$, and constants such as $$\frac{\sqrt{2}}{2}$$

due to the geometry of the sensor). As is apparent from the equations immediately above, normal force $F_z$ can be obtained by averaging all four time-of-flight measurements from one sensor unit. The averaging process will increase the accuracy of the calculated value of $F_z$. Further, since differential time intervals are used in calculating the value of the two shear force components, the calculation can be made independent of temperature effects on the elastomer. The primary effect of temperature on the sensor is to cause the elastomer to expand and the speed-of-sound to decrease with an increase in temperature. Secondarily, elastomer stiffness also decreases somewhat with increasing temperature. If the above shear force equations are modified slightly by dividing the time difference by the sum of the two time intervals (e.g., $(t_1-t_3)/(t_1+t_3)$), then the effects of temperature on rubber thickness and speed-of-sound are eliminated.

While not set forth in detail, it will be readily understood that, through use of at least three basic sensor units 50 (either three- or four-transducer configuration) in a common plane and non-colinearly arranged, the three torque components $M_x$, $M_y$ and $M_z$ may be calculated from the difference in the force components at the three sensor unit sites.

Referring now to FIGS. 17 through 39 of the drawings, additional preferred and alternative embodiments of the sensor of the present invention are depicted, as basic sensor units and as multi-unit sensor arrays.

Figure 17:
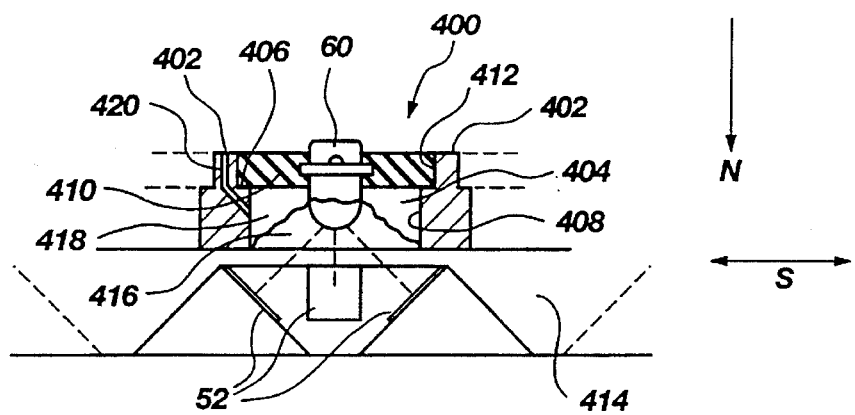
FIG. 17 is a schematic, partial sectional side elevation of yet another preferred configuration for a basic sensor unit.

FIG. 17 schematically depicts basic sensor unit 400, which is combined with other, like units 400 to define a multi-unit sensor array as subsequently described. Sensor unit 400 includes rigid support member 402, which may comprise steel, aluminum, bronze or other suitable metal, or a rigid, substantially incompressible nonmetallic material. The degree of rigidity required is naturally dependent upon the forces to which sensor unit 400 is subjected. Support member 402, as shown, may comprise part of a larger support member for an array of sensor units, or may comprise a free-standing support structure, as desired. Support member 402 includes an aperture 404 therethrough, aperture 404 preferably being of a counterbore configuration with upwardly-facing shoulder 406 extending substantially continuously about bore wall 408. Aperture 404 may be of square, circular or other suitable cross-sectional shape.

Target 60, which in this instance comprises a bullet-shaped steel pin with a hemispherical lower end, is suspended in aperture 404 by a biasing element 410, which may comprise any suitable elastomer, spring or other biasing structure, as will be described hereafter in more detail. In FIG. 17, biasing element 410 comprises an elastomeric ring, for exemplary purposes only. If target 60 is employed with an elastomeric biasing element, it may include a flange, transversely-extending protrusions or other structure as shown to engage the elastomer body and prevent slippage when force is applied to the sensor unit 400. Biasing element 410 is supported about its periphery against normal forces by shoulder 406, and against shear forces by the upper portion 412 of bore wall 408. Support member 402 is oriented over angled transducers 52 aimed at the lower end of target 60.

As with previously-described variations of the invention, it is preferable to employ four transducers with each target, although three may suffice. Transducers 52 are preferably bedded or potted in a hard, substantially noncompliant silicone rubber layer 414 for protection against mechanically or chemically-caused damage. A much softer, very compliant silicone rubber or gel mass 416 is disposed in cavity 418 between target 60 and layer 414 to facilitate unrefracted acoustic transmission between transducers 52 and the lower face of target 60. Mass 416 provides no support to target 60 against either shear or normal forces, and need not be bonded to layer 414. At least a portion of cavity 418 remains empty, to accommodate free downward movement of target 60 and biasing element 410. It is also preferable that cavity 418 be vented as at 420, to prevent trapped, compressed air from augmenting the design biasing characteristics of biasing element 410. While support member 402 may rest on silicone rubber layer 414, it is preferably that it be independently supported and suspended above layer 414 and transducers 52 for greater stiffness and maximum accuracy.

Figure 18:
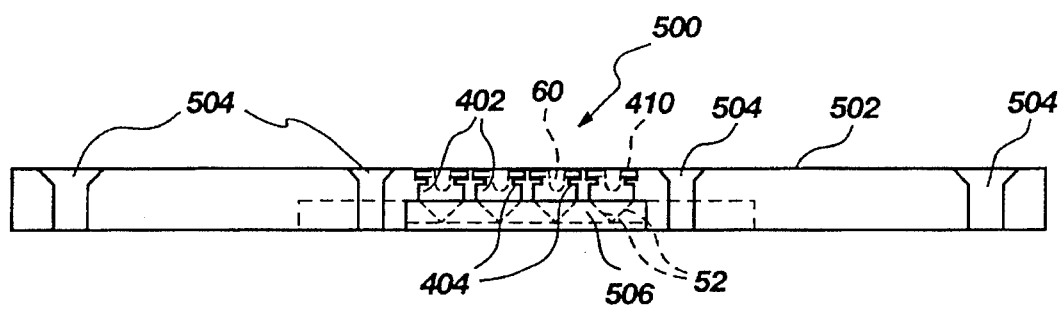
FIGS. 18 and 19 are, respectively, a side sectional elevation and a bottom elevation of a rigid support member suitable for use in a multi-sensor unit array according to the present invention.
Figure 19:
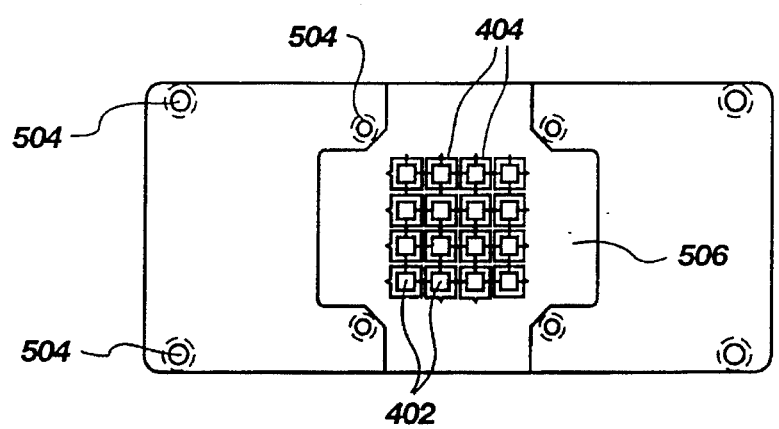

FIGS. 18 and 19 depict a rigid planar support member 502 for a 4×4 array 500 of basic sensor units 400. Four columns and four rows of square apertures 402 having shoulders 406 are depicted, although arrays with more or fewer sensor units 400, or different numbers of sensor units 400 in the rows and columns are also contemplated, as are arrays with sensor units 400 disposed in radial, circular or other patterns as desired. Planar support member 502 includes a plurality of fastener bores 504 for securing member 502 to an underlying rigid substrate (not shown) such as a floor, platform, roadbed or other structure. As shown in FIGS. 18 and 19, transducer cavity 506 is machined or otherwise formed in the bottom of member 502 to accommodate an array of transducers 52 to be associated and aligned with targets 60 and biasing elements 410, one target/biasing element assembly being disposed in each aperture 402. It will be appreciated that support member 502 will rigidly and precisely suspend targets 60 via their individual biasing elements 410 above the transducer array at stable, repeatable rest positions. Further, high lateral or shear forces may be accommodated using this design. While extremely high loading forces may result in flexing cross-talk between adjacent sensor units 400 with this design, the use of a metal plate having predictable elastic deformation characteristics permits electronic compensation for such phenomena during signal processing. In addition, use of a multi-apertured support member 502 facilitates repair and replacement of targets and biasing members, as well as permitting ready access to the underlying transducer array.

Figure 20:
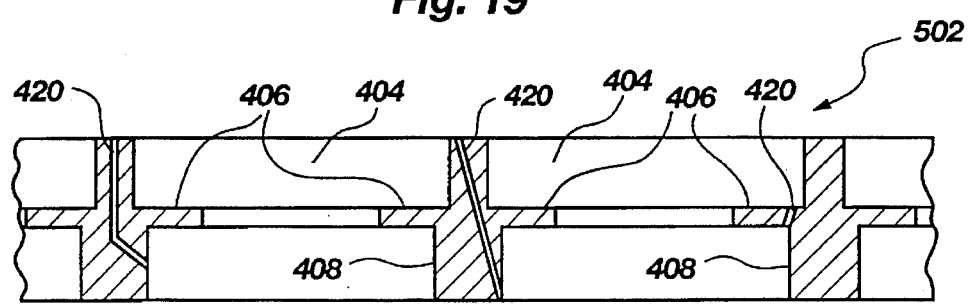
FIG. 20 is an enlarged side sectional elevation of a portion of the support member of FIGS. 18 and 19.
Figure 26:
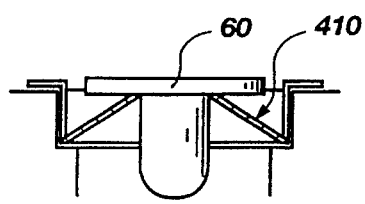
FIGS. 26–36 comprise additional side elevations of alternative metal and combined metal/elastomer target biasing elements suitable for use in the present invention.
Figure 27:
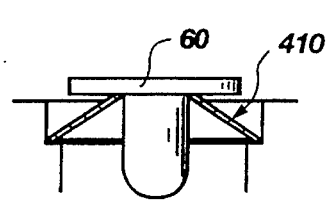
Figure 28:
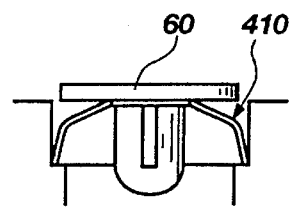
Figure 29:
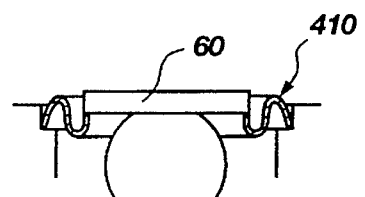
Figure 30:
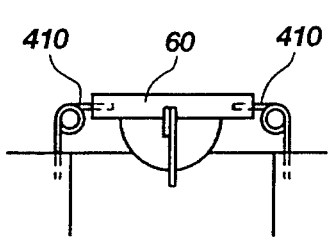
Figure 31:
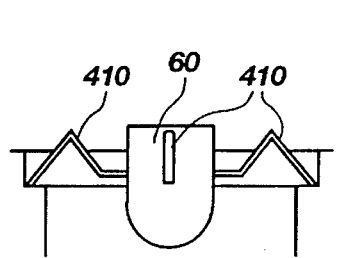
Figure 32:
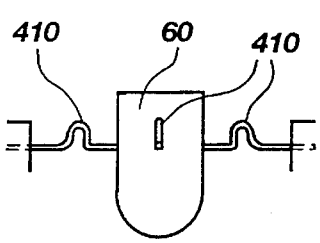
Figure 33:
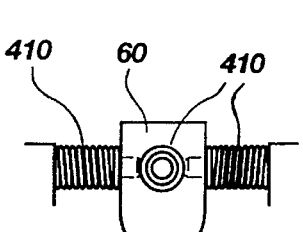
Figure 36:
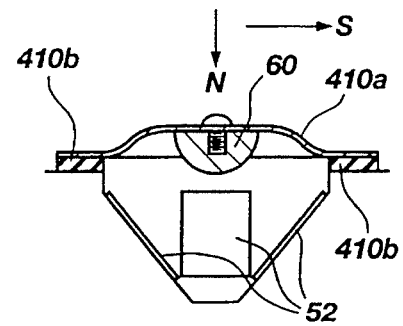

FIG. 20 depicts a plurality of adjacent apertures 404 in support member 502, showing borewalls 408, shoulders 406 and various styles of vents 420. FIG. 21 depicts three targets 560 of yet another configuration, supported in three apertures 402 in support member 502 by biasing elements 510, also of a different configuration from those previously described. FIG. 22 comprises a partial side sectional elevation of target 560 supported by element 510 in an aperture 402.

Target 560 includes a lower hemispherical portion 562 which comprises the actual target location toward which ultrasonic waves are projected by transducers 52. Medial square plate portion 564 extends laterally beyond lower portion 562 to define target support flange 566, and upwardly to define target support surface 568. Plate portion 564 is surmounted by upper frustoconical portion 570, to facilitate point loading of target 560 by the element (shoe, fire, etc.) applying a force to the sensor array and reduce any tendency of the target to "rock" due to off-center loading. If desired, a center vertical bore 572 may be formed in target 560, for calibration purposes.

Biasing element 510 comprises an upper, larger elastomer square 512 and a lower, smaller elastomer square 514 which are preferably integrally formed and interconnected along line 516 by a small web of material. Target 560 is placed within biasing element 510 so that support flange 566 rests upon lower square 514 and lower portion 562 protrudes therethrough, while support surface 568 is surrounded by upper ring 512. If desired, target 560 may be molded into biasing element 510 during fabrication of the latter. Venting of ring aperture 574 is desirable to prevent possible air trapping and compression, as previously noted with respect to cavity 418.

It will be appreciated that, unlike the configuration of FIG. 17, wherein the biasing element 410 is placed in shear during the application of a normal force N to the sensor unit 400 and in compression during the application of a shear force S, cooperative configurations of target 560 and biasing element 510 ensure that both normal forces N and shear forces S will respectively place lower ring 514 and upper ring 512 in compression. Thus, in the latter case, the biasing response to both normal and shear forces will be more predictable, and close to the same if both rings are of the same cross section as shown, and made of the same elastomer. It is also contemplated that rings 512 and 514 may intentionally be made of different cross-sectional size or configuration, or of elastomers with different durometer ratings, such as two different polyurethanes, in order to custom-tailor the sensor unit's response to applied forces. Similarly, elastomer durometer ratings ranging from very hard to very soft are easily achievable with silicone rubbers, polyurethanes and other elastomers known in the art, so that a sensor may be caused to respond with the sensitivity desired for a particular range of loading. Thus, the same basic sensor array might be employed with one selection of biasing elements 510 to accurately determine forces applied by the foot of a person, and with another selection of elements 510 to determine loads applied by a motor vehicle. Similarly, the upper portions 570 of targets 560 may be configured in various manners to provide greater or lesser frictional engagement with the intended force-applying element, and may be coated or plated with different materials to enhance or reduce friction.

FIGS. 23 through 25 show additional alternative configurations and arrangements of targets 60, support members 402 and elastomeric biasing elements 410 which are configured to place the biasing elements in compression under both normal and shear loading. However, it is believed that these arrangements may be subject to hysteresis problems due to measurable internal shear within the bodies of elements 410.

As noted above, biasing elements 410 may comprise metallic springs or spring-like elements, or combinations of elements, both metallic and non-metallic. FIGS. 26–36 depict numerous such alternative variations of target and biasing element assemblies, each of which may comprise a preferred arrangement for a particular force measurement function.

Figure 34:
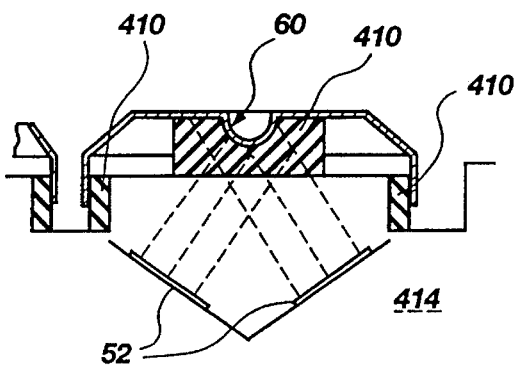
Figure 35:
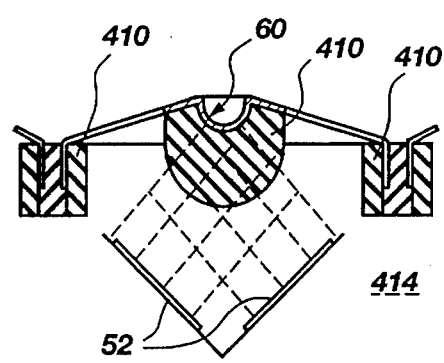

FIGS. 26–33 depict the use of metal biasing elements 410 of various configurations, it being understood that resilient or "springy" materials such as hard plastic or fiberglass, or composite materials such as laminated carbon fibers, may also be employed where desired in lieu of spring steel or other metal. The particular material employed to achieve the spring effect in FIGS. 26–33 is limited only by one's ability to fabricate the spring element from a particular material. FIGS. 34 and 35, unlike FIGS. 26–33, employ the resiliency of a compressible material such as a urethane or rubber to respond to both shear and normal forces, the metallic component of the assembly providing a target 60 and a linkage between the target 60, the compressible elements 410 and the supporting structure, and may only incidentally provide some biasing effect. The structure of FIG. 36 employs both metal and resilient elastomer active biasing elements. A spring steel plate 410a is used to respond in flexure to normal forces N, while an elastomer layer or elements 410b is used to provide a bias against shear forces S. As shown, the target 60 may be affixed to plate 410a via a screw or rivet, as desired. Plate 410a may be flat, but is preferably of bowed configuration as shown, and may include features of the biasing elements 410 of FIGS. 26–33. The use of an elastomeric element placed in shear (rather than compression) as a biasing element has demonstrated a significant reduction in hysteresis in testing (on the order of 50%), and may be considered as a preferred structural implementation of the present invention for some applications.

It is noted that FIGS. 34 and 35, which employ a rigid shell supported from below and laterally by rubber or other suitable elastomer, may be employed without a rigid support member such as 402 or 502, as they might rest on and be constrained by protrusions in an underlying hard rubber layer such as 414. It is further noted that the arrangement of FIG. 35 may be subject to cross-talk between adjacent sensor units 400 in an array 500, due to the presence of foam rubber in the inter-protrusion valleys between the rigid shells.

Figure 37:
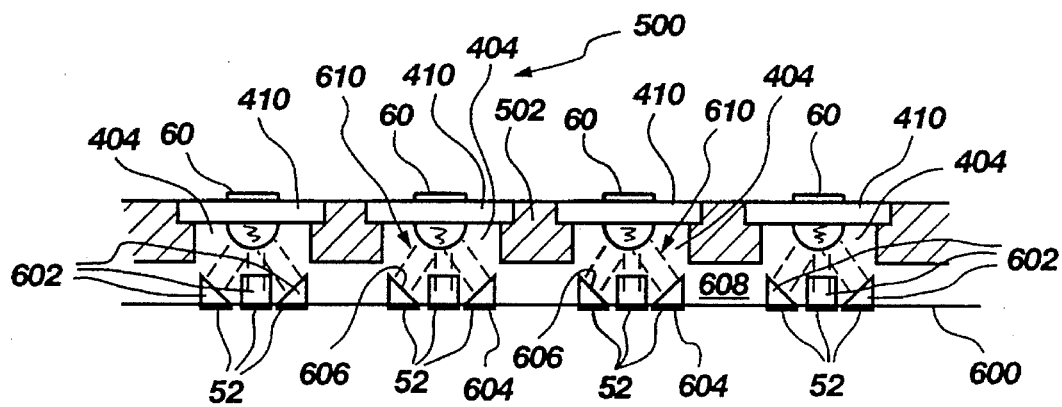
FIG. 37 is a schematic partial sectional side elevation of a preferred transducer arrangement employing acoustic prisms to refract ultrasound waves travelling to and from targets.

Yet another feature of the invention which has particular utility in the formation of a sensor array 500 is the disposition of transducers 52 in a horizontal position parallel to the plane of the array 500, and the use of acoustically refractive elements or prisms to reorient the ultrasonic waves directed to and reflected from targets 60. FIG. 37 schematically depicts such an arrangement as employed with a rigid support member 502, targets 60 and biasing elements 410 being disposed in apertures 402. Transducers 52, of the aforementioned PVDF film, lie in a horizontal plane 600 and are aimed vertically upward. Acoustic prisms 602, each of nylon, polyethylene or other suitable acoustically refractive material which is highly transparent to ultrasound, are placed over each transducer 600 to refract transduceremitted sound waves 610. Prisms 602 each include a flat lower surface 604 disposed over a transducer 52, and an angled surface 606 disposed at a selected angle to the horizontal. Each prism 602 refracts the emitted sound waves from a vertical or perpendicular orientation to the transducer plane to an angle perpendicular to angled surface 606 and refracts the returning sound waves reflected from targets 60 back to a vertical orientation and onto the emitting transducer 52, as shown. This configuration permits more inexpensive fabrication of transducer arrays with more precise transducer placement, and also permits closer spacing of basic sensor units so that more of same may be placed per unit area within an array.

Sound waves emitted by transducers 52 and refracted by prisms 602 are preferably conducted between prism faces 606 and targets 60 through a very soft or compliant layer or masses 608 of silicone rubber, which may even comprise an unset gel rather than a cohesive mass. As previously noted, silicone rubber is a desirable acoustic coupling material due to the relatively low speed of sound c therethrough, on the order of 1,000 meters per second (m/s), which provides enhanced resolution. By way of comparison, c for urethanes range from about 1,500 to 1,800 m/s, for polyethylene c is about 2,000 m/s, and for nylon c is about 2,600 m/s. As noted previously, it is undesirable for the transmission mass or layer 608 to provide any support for targets 60, as such support would have to be factored in to the force measurements attributable to differences in wave travel time responsive to change in target position under force. It will be appreciated that a fluid coupling medium, such as silicone oil, may also be employed in lieu of solid or gel couplants, with appropriate containment structure.

Figure 38:
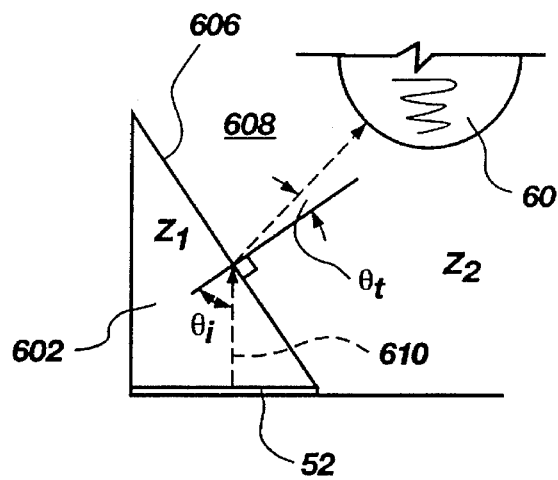
FIG. 38 is a schematic depiction of the refraction of sound waves travelling between a transducer and a target through an acoustic prism and adjacent transmitting medium.

In selecting appropriate materials for prisms 602 and coupling layer or masses 608, the speed of sound $c_1$ in the prism material should exceed that ($c_2$) in the mass material. Further, the mass density $\rho_1$ of the prism material should be less than that ($\rho_2$) of the mass or layer material. FIG. 38 of the drawings depicts a transducer 52 aimed into an acoustic prism 602 with a couplant mass 608 interposed between prism surface 606 and target 60. With reference to the angular relationships shown in FIG. 38, for minimum reflectivity as acoustic wave 610 travels between transducer 52 and target 60, $$Z_2 \cos \theta_i = Z_1 \cos \theta_t$$

where $Z_1$ equals the acoustic impedance of the prism material 602 ($c_1 \times \rho_1$) and $Z_2$ equals the acoustic impedance of the couplant material 608 ($c_2 \times \rho_2$), $\theta_i$ is the sound wave angle of incidence from transducer 52 through prism 602 with respect to a normal to the line of intersection between prism and couplant material, and $\theta_t$ is the sound wave angle of transmission through the couplant 608 with respect to the normal line. It will be appreciated that, while exact equality in the above relationship is desirable, as a practical matter such is difficult to achieve.

Figure 39:
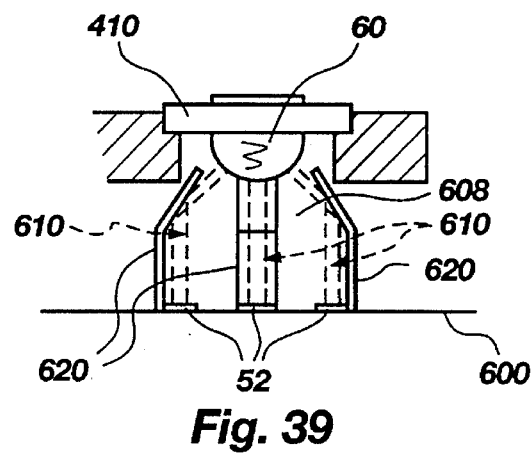
FIG. 39 is a schematic partial sectional side elevation of an alternative transducer arrangement employing acoustic reflectors to reorient ultrasound waves travelling to and from targets.

Yet another variation of the invention is illustrated in FIG. 39 of the drawing wherein, as in FIG. 37, transducers 52 are placed in a plane 600 and aimed perpendicularly upward with respect thereto. However, in lieu of acoustic prisms 602, acoustic reflectors 620 of metal or metallized plastic, are employed to reflect vertical sound waves 610 toward targets 60 and returning sound waves back to transducers 52. Any suitable metal or metal coating may be employed, such as steel, aluminum, brass or other ferrous and non-ferrous metals. A grid of such reflectors 620 with highly accurate reflector locations and angles may be molded from plastic and then metallized using techniques well-known in the art. As with the embodiment of FIG. 36, a highly acoustic transmissive layer or masses 608 are employed between transducers 52 and targets 60.

In fabrication of basic sensor units or arrays to accommodate particular space limitations or configurations or sensor or array topography, it may be desirable or even necessary to combine directly-aimed transducers with transducers aimed through acoustic prisms or by acoustic reflectors or prism-aimed transducers with reflector-aimed transducers. With appropriate mathematic processing to accommodate different distances and speeds of sound through materials, such an arrangement is within the ability of one of ordinary skill in the art and is contemplated as within the scope of the invention.

While the present invention has been described in terms of the illustrated embodiments, those of ordinary skill in the art will readily understand and appreciate that it is not so limited. Many additions, deletions and modifications to the embodiments illustrated and described herein are possible without departing from the scope of the invention as hereinafter claimed.

What is claimed is:

1. A sensor for use in determining shear and normal components of a force applied thereto, comprising:

a substantially rigid support member carrying a compliant structure;

at least one target for reflecting ultrasonic waves supported by said compliant structure;

at least two ultrasonic transducers aimed at said target, each of said transducers adapted to emit and detect ultrasonic signals, said transducers being laterally and vertically offset from said at least one target; and a substantially acoustically-transparent, substantially acoustically-nonrefractive medium disposed between said transducers and said at least one target.

2. The sensor of claim 1, wherein said at least two transducers are located in a common plane.

3. The sensor of claim 1, wherein said at least two transducers comprises four transducers located at 90° intervals around said target.

4. The sensor of claim 1, wherein said target presents a constant-radius, arcuate, reflective surface to said transducers.

5. The sensor of claim 1, wherein said target is at least partially embedded in said compliant structure.

6. The sensor of claim 5, wherein said compliant structure comprises an elastomer.

7. The sensor of claim 6, wherein said elastomer is selected from a group comprising urethanes, silicone rubbers, neoprene rubbers, natural rubbers, plastics, and gels.

8. The sensor of claim 1, wherein said compliant structure comprises a metal spring structure.

9. The sensor of claim 1, wherein said compliant structure comprises a combined metal and elastomer spring structure.

10. The sensor of claim 1, wherein said at least two transducers are embedded in an elastomer layer, said layer comprising a portion of said substantially acoustically-transparent, substantially acoustically-nonrefractive medium.

11. The sensor of claim 1, further comprising a displaceable medium disposed between said at least two transducers and said target, said displaceable medium comprising a portion of said substantially acoustically-transparent, substantially acoustically-nonrefractive medium.

12. The sensor of claim 1, wherein said transducers are selected from a group comprising PVDF films and ceramics.

13. The sensor of claim 1, wherein said substantially rigid support member includes an aperture therein, said compliant structure is supported by said support member along at least a portion of the periphery of said aperture, and said target is suspended within said aperture by said compliant structure.

14. The sensor of claim 1, wherein said substantially rigid support member includes an aperture therein, said aperture is symmetric in shape, and said target is supported in the center of said aperture.

15. The sensor of claim 1, wherein said at least two transducers are located in a common plane, at least one of said at least two transducers is oriented to emit said ultrasonic signals perpendicular to said common plane, and wherein said sensor further includes angle-changing structure for aiming said perpendicularly emitted ultrasonic signals at said target by changing the angle of said emitted ultrasonic signals after emission from said at least one oriented transducer and for changing the angle of said ultrasonic waves after reflection from said target to the perpendicular to said common plane for detection by said at least one oriented transducer.

16. The sensor of claim 15, wherein said angle-changing structure comprises an acoustic prism.

17. The sensor of claim 15, wherein said angle-changing structure comprises an acoustic reflector.

18. The sensor of claim 1, wherein at least one of said transducers is aimed at said target through an acoustic prism placed therebetween.

19. The sensor of claim 1, wherein at least one of said transducers is aimed at said target via an acoustic reflector.

20. A multi-sensor array for use in determining shear and normal components of a force applied thereto, comprising:

a substantially rigid support member carrying a plurality of laterally separated compliant structures located at predetermined intervals;

a plurality of targets for reflecting ultrasonic waves, each of said targets being supported by one of said compliant structures;

each of said targets having associated therewith at least a pair of ultrasonic transducers adapted to emit and receive ultrasonic signals, said transducers of each pair being aimed at said target with which said transducers are associated and horizontally and vertically offset therefrom; and a substantially acoustically-transparent, substantially acoustically-nonrefractive medium disposed between said transducers and said targets.

21. The multi-sensor array of claim 20, wherein said targets are located at substantially equal intervals and in a common plane.

22. The multi-sensor array of claim 20, wherein said transducers are located in a common plane.

23. The multi-sensor array of claim 20, wherein said at least a pair of transducers comprises four transducers located at 90° intervals around each of said targets.

24. The multi-sensor array of claim 20, wherein said targets each present a constant-radius, arcuate, reflective surface to the transducers associated therewith.

25. The multi-sensor array of claim 20, wherein at least some of said targets are embedded in said compliant structures.

26. The multi-sensor array of claim 25, wherein said compliant structures comprise an elastomer.

27. The multi-sensor array of claim 26, wherein said elastomer is selected from a group comprising urethanes, silicone rubbers, neoprene rubbers, natural rubbers, plastics and gels.

28. The multi-sensor array of claim 20, wherein said compliant structures comprise metal spring structures.

29. The multi-sensor array of claim 20, wherein said compliant structures comprise combined metal and elastomer spring structures.

30. The multi-sensor array of claim 20, wherein said transducers are embedded in an elastomer layer, said layer comprising at least a portion of said substantially acoustically-transparent, substantially acoustically-nonrefractive medium.

31. The multi-sensor array of claim 20, further comprising a displaceable medium disposed between said transducers and said targets, said displacable medium comprising a portion of said substantially acoustically-transparent, substantially acoustically-nonrefractive medium.

32. The multi-sensor array of claim 20, wherein said transducers are selected from a group comprising PVDF films and ceramics.

33. The multi-sensor array of claim 20, wherein said substantially rigid support member includes a plurality of apertures therein, each of said compliant structures is supported by said support member along at least a portion of the periphery of one of said apertures, and said targets are suspended within said apertures by said compliant structures.

34. The multi-sensor array of claim 20, wherein said substantially rigid support member includes a plurality of apertures therein, said apertures are symmetric in shape, and said targets are supported in the centers of said apertures.

35. The multi-sensor array of claim 20, wherein said transducers are located in a common plane, at least one of said transducers is oriented to emit said ultrasonic signals perpendicular to said common plane, and further including structure for aiming said perpendicularly emitted ultrasonic signals at the target with which said at least one oriented transducer is associated by changing the angle of said perpendicularly emitted ultrasonic signals after emission and for changing the angle of said ultrasonic waves after reflection from said target to the perpendicular to said common plane for detection by said at least one oriented transducer.

36. The multi-sensor array of claim 35, wherein at least one of said angle-changing structures comprises an acoustic prism.

37. The multi-sensor array of claim 35, wherein at least one of said angle-changing structures comprises an acoustic reflector.

* * * * *

UNITED STATES PATENT AND TRADEMARK OFFICE
CERTIFICATE OF CORRECTION

PATENT NO. : 5,604,314                                  Page 1 of 2
DATED      : February 18, 1997
INVENTOR(S): Allen R. Grahn It is certified that error appears in the above-identified patent and that said Letters Patent is hereby corrected as shown below: ON THE TITLE PAGE:

Under "Other Publications" on line 3 "Finger" should be --Fingertip--.
On the Title Page, under "Other Publications" on line 3, after "Tactile" insert --Sensor--;

On the Title Page, under "Other Publications" delete the duplicate listing of Hackwood, S. and insert the following --Grupen, R.A., et al., A Survey of General Purpose Manipulation, International Journal of Robotics Research, Vol. 8. No. 1, Feb. 1989--.

On the Title Page under Assignee insert the following: [*] Notice: The term of this patent shall not extend beyond the expiration date of Pat. No. 5,553,500.

In column 2, line 4, change "free" to --fine--

In column 4, line 7, change "fines" to --lines--

In column 4, line 59, change "sa" to --a--

In column 6, line 54, 55, change ", and $_2$" to --$t_1$ and $t_2$--

In column 7, line 60, change "are carded" to --is carried--

In column 7, line 62, change "are carded" to --is carried--

In column 8, line 29, after "medium" insert --,-- (comma)

In column 8, line 35, after "multi-sensor" delete --,-- (comma)

In column 9, line 9, at the beginning of the line, delete -- - -- (dash)

In column 10, line 61, change "proCessing" to --processing--

In column 13, line 45, change "time" to --times--

In column 14, line 9, after "depicted" delete --,-- (comma)

In column 14, line 55, after "empty" delete --,-- (comma)

In column 14, line 57, after "420" delete --,-- (comma)

In column 14, line 60, change "preferably" to --preferable--

In column 14, line 63, after "rigid" insert --,-- (comma)

UNITED STATES PATENT AND TRADEMARK OFFICE
CERTIFICATE OF CORRECTION

PATENT NO. : 5,604,314
DATED : February 18, 1997
INVENTOR(S) : Allen R. Grahn

It is certified that error appears in the above-identified patent and that said Letters Patent is hereby corrected as shown below:

In column 15, line 29, change "402" to --404--

In column 15, line 33, change "402" to --404--

In column 15, line 40, after "570" delete --,-- (comma)

In column 15, line 42, change "fire" to --tire--

In column 15, line 45, after "560" delete --,-- (comma)

In column 16, line 65, after "that" insert --the arrangements of--

In column 17, line 20, change "600" to --52--

In column 17, line 42, change "range" to --ranges--

In column 18, line 4, change "0$_i$" to --0$_t$--

In column 18, line 7, after "matter" insert --,-- (comma)

In column 18, line 13, after "plastic" delete --,-- (comma)

In column 18, line 15, change "returning" to --return--

In column 18, line 21, change "36" to --38--

In column 18, line 59, change "comprises" to --comprise--

Signed and Sealed this

Twenty-fourth Day of November, 1998

Attest:

BRUCE LEHMAN

*Attesting Officer*  Commissioner of Patents and Trademarks